(12) United States Patent
Dickerson

(10) Patent No.: US 10,321,930 B2
(45) Date of Patent: Jun. 18, 2019

(54) ACTIVATION FEATURES FOR ULTRASONIC SURGICAL INSTRUMENT

(71) Applicant: Ethicon Endo-Surgery, LLC, Guaynabo, PR (US)

(72) Inventor: Benjamin D. Dickerson, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 667 days.

(21) Appl. No.: 14/833,288

(22) Filed: Aug. 24, 2015

(65) Prior Publication Data

US 2017/0056050 A1    Mar. 2, 2017

(51) Int. Cl.
*A61B 17/32*  (2006.01)
*A61B 17/00*  (2006.01)
*A61B 17/29*  (2006.01)

(52) U.S. Cl.
CPC ........... *A61B 17/320068* (2013.01); *A61B 2017/00017* (2013.01); *A61B 2017/00367* (2013.01); *A61B 2017/2918* (2013.01)

(58) Field of Classification Search
CPC ............. A61B 17/320068; A61B 2017/00367; A61B 2017/00017; A61B 2017/2918
See application file for complete search history.

(56) References Cited

U.S. PATENT DOCUMENTS

| | | |
|---|---|---|
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |

(Continued)

FOREIGN PATENT DOCUMENTS

| | | |
|---|---|---|
| DE | 24 60 481 A1 | 6/1976 |
| EP | 2 298 197 A2 | 3/2011 |
| WO | WO 2008/089174 A2 | 7/2008 |

OTHER PUBLICATIONS

U.S. Appl. No. 61/410,603, filed Nov. 5, 2010.
International Search Report and Written Opinion dated Nov. 3, 2016 for Application No. PCT/US2016/048193, 13 pgs.

*Primary Examiner* — Diane Yabut
(74) *Attorney, Agent, or Firm* — Frost Brown Todd LLC

(57) ABSTRACT

An ultrasonic instrument includes a body, an actuation assembly, a shaft assembly, and an ultrasonic blade. The body defines a longitudinal axis and is configured to receive an ultrasonic transducer. The actuation assembly includes at least one annular activation member and at least one circuit. The at least one annular activation member extends angularly about the body along a 360 degree angular range. The at least one annular activation member is configured to move laterally relative to the longitudinal axis of the body. The at least one circuit corresponds to the at least one annular activation member. The shaft assembly includes an acoustic waveguide. The ultrasonic blade is in acoustic communication with the acoustic waveguide. The at least one activation circuit is configured to activate the ultrasonic blade in response to lateral movement of the activation member relative to the longitudinal axis of the body.

20 Claims, 24 Drawing Sheets

(56) References Cited

U.S. PATENT DOCUMENTS

| | | |
|---|---|---|
| 6,773,444 B2 | 8/2004 | Messerly |
| 6,783,524 B2 | 8/2004 | Anderson et al. |
| 7,530,987 B1 * | 5/2009 | Hausen .............. A61B 17/3211 606/170 |
| 8,057,498 B2 | 11/2011 | Robertson |
| 8,152,825 B2 | 4/2012 | Madan et al. |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,241,732 B2 | 1/2016 | Craig |
| 9,381,058 B2 | 7/2016 | Houser et al. |
| 9,393,037 B2 | 7/2016 | Olson et al. |
| 2002/0049464 A1 * | 4/2002 | Donofrio ....... A61B 17/320068 606/169 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2015/0080924 A1 | 3/2015 | Stulen et al. |
| 2015/0148829 A1 | 5/2015 | Kimball et al. |
| 2016/0106455 A1 | 4/2016 | Aldridge et al. |

\* cited by examiner

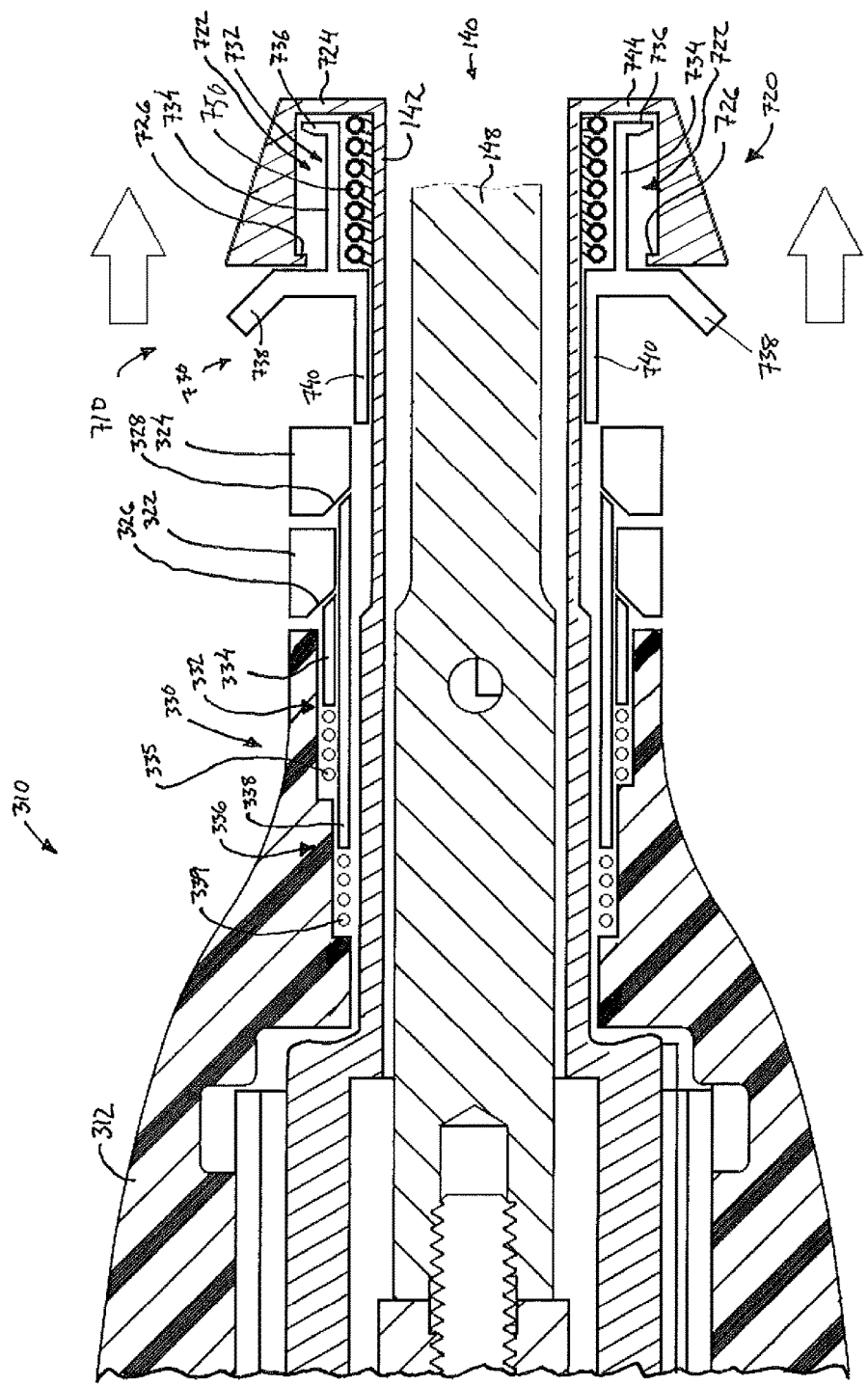

ACTIVATION FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May. 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, the disclosure of which is incorporated by reference herein; U.S. Pub. No. 2012/0116265, issued as U.S. Pat. No. 9,381,058 on Jul. 5, 2016, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,037 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 24 depicts another side cross-sectional view of the handle assembly of FIG. 22, with a lock assembly in an unlocked position.

Figure 1:
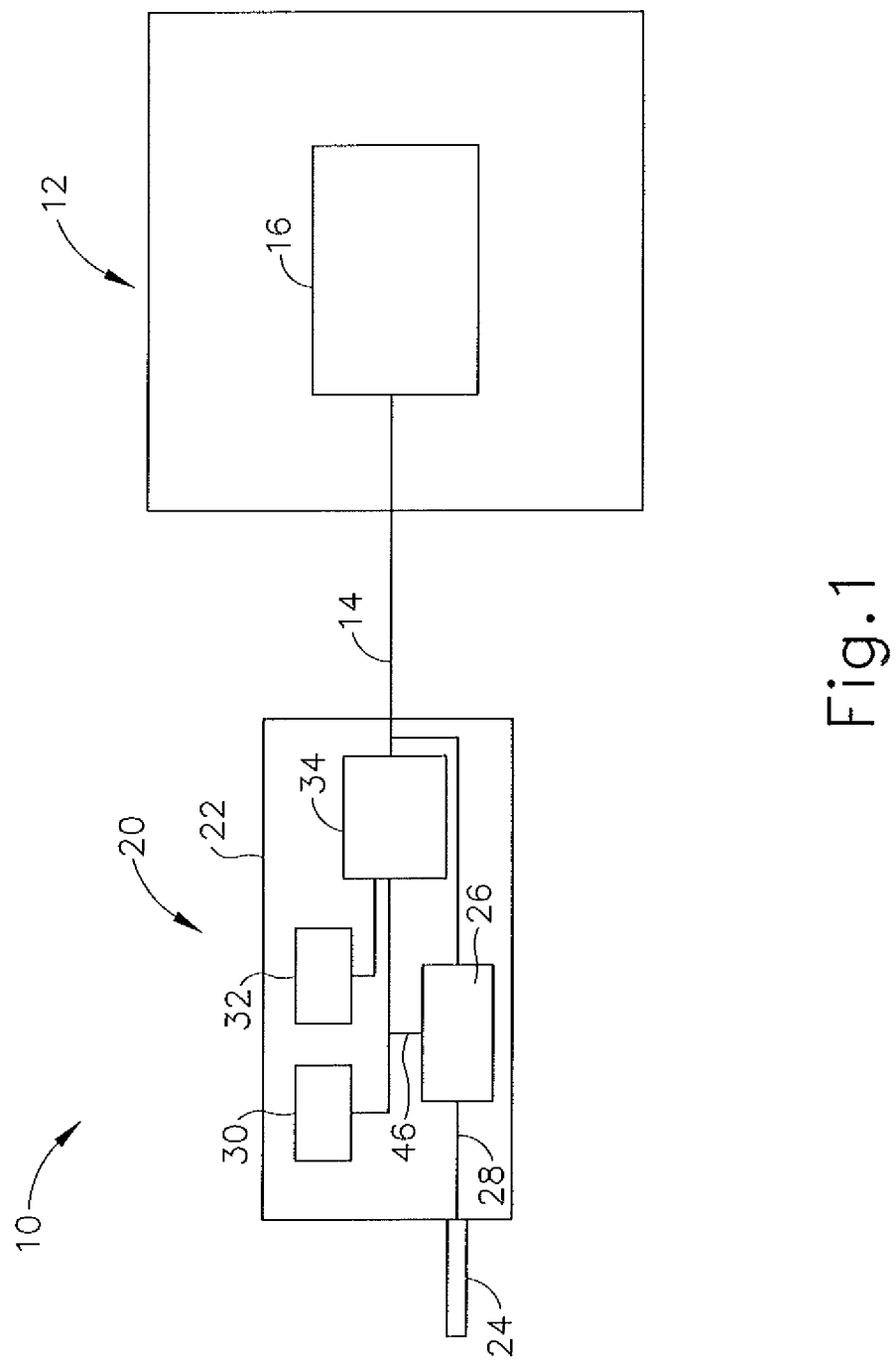
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. By way of example only, instrument (20) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2015/0080924, issued as U.S. Pat. No. 10,172,636 on Jan. 8, 2019; and/or U.S. Pat. App. No. 61/410,603.

The disclosures of each of the foregoing patents, publications, and applications are incorporated by reference herein.

It should also be understood that instrument (20) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (20) may have various structural and functional similarities with the devices taught in any of the other references that are cited and incorporated by reference herein. To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (20), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures. It should also be understood that some versions of system (10) may incorporate generator (12) into instrument (20), such that cable (14) may simply be omitted.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (e.g., via remote control, etc.).

In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
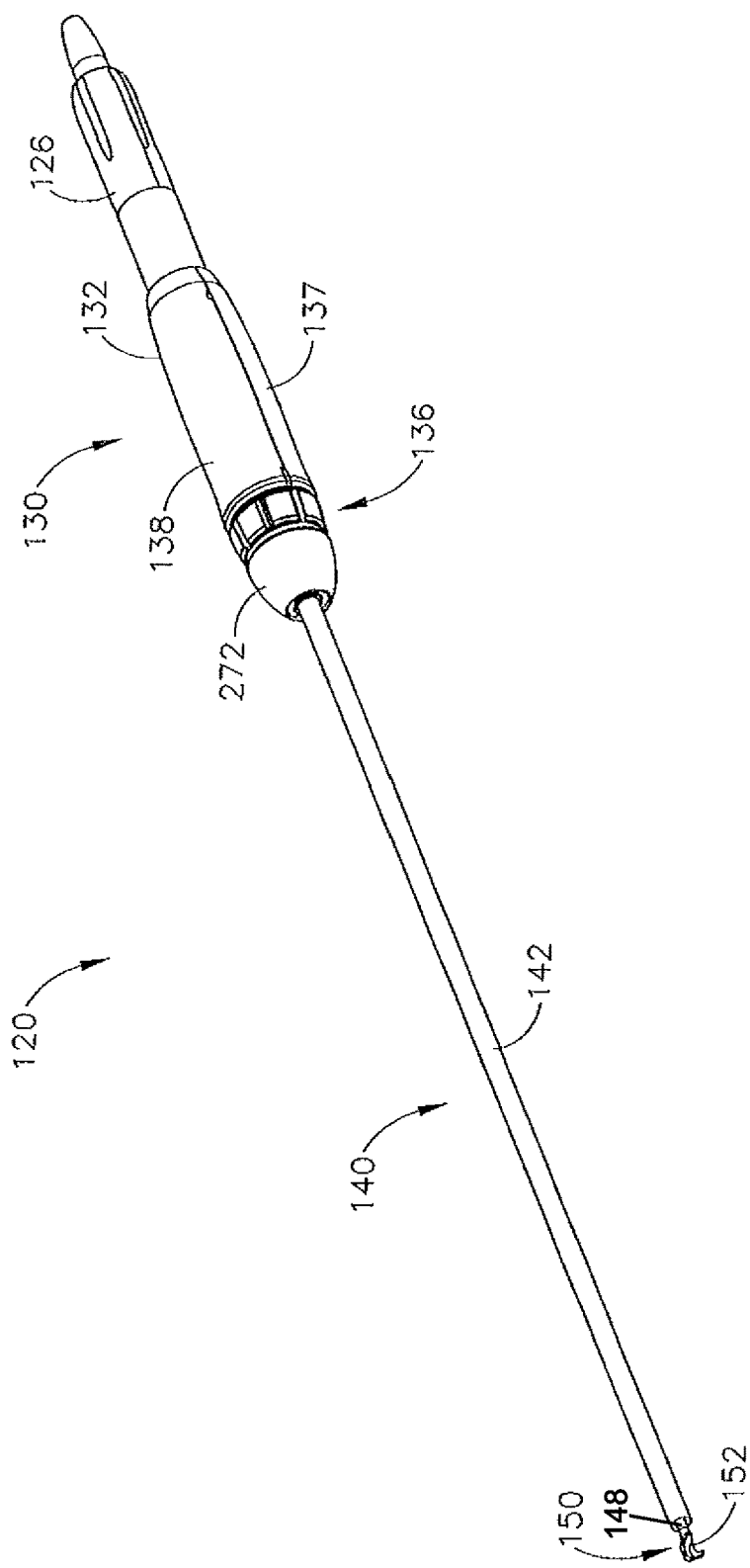
FIG. 2 depicts a perspective view of an exemplary surgical instrument that may be incorporated into the system of FIG. 1.

FIG. 2 illustrates an exemplary ultrasonic surgical instrument (120) that may be used as instrument (20) of system (10) described above. At least part of instrument (120) may therefore be constructed and operable in accordance with at least some of the teachings above with respect to instrument (20). As with instrument (20), instrument (120) is operable to cut tissue and seal or weld tissue (e.g., a blood vessel, etc.) substantially simultaneously. Instrument (210) of this example is configured to be used as a scalpel. As will be described in greater detail below, instrument (120) provides enhanced access to activation features.

As shown in FIG. 2, instrument (120) of this example comprises a handle assembly (130), a shaft assembly (140), and an end effector (150). The proximal end of instrument (120) receives and is fitted with an ultrasonic transducer (126) by insertion of ultrasonic transducer (126) into handle assembly (130). Handle assembly (130) is configured to receive ultrasonic transducer (126) such that ultrasonic transducer (126) may be coupled to a waveguide (148) in shaft assembly (140) by a threaded connection, though any other suitable type of coupling may be used. As shown, instrument (120) may be coupled with ultrasonic transducer (226) to form a single unit.

Shaft assembly (140) comprises an outer sheath (142) and a waveguide (148) disposed within outer sheath (142). In some versions, outer sheath (142) and waveguide (148) are sized to fit through a trocar or other minimally invasive access port, such that instrument (120) may be used in a minimally invasive surgical procedure. Waveguide (148) is configured to transmit ultrasonic vibrations from transducer (126) to an ultrasonic blade (152). Waveguide (148) may be flexible, semi-flexible or rigid. Waveguide (148) may also be configured to amplify the mechanical vibrations transmitted through waveguide (148) to blade (152). Waveguide (148) may further include at least one bore (not shown) extending therethrough, substantially perpendicular to the longitudinal axis of waveguide (248). The bore may be located at a longitudinal position corresponding to a node associated with ultrasonic vibrations communicated along waveguide (148). The bore may be configured to receive a connector pin (not shown) that connects waveguide (148) to outer sheath (142). Since the connector pin would be located at a nodal position, the pin would not transmit ultrasonic vibrations from waveguide (148) to outer sheath (142); yet the connector pin may still provide a longitudinal and rotational ground for outer sheath (142).

Blade (152) may be integral with the ultrasonic waveguide and formed as a single unit. In some versions, blade (152) may be connected to waveguide (148) by a threaded connection, a welded joint, and/or some other coupling feature(s). The distal end of blade (152) is disposed at or near a longitudinal position corresponding to an anti-node associated with ultrasonic vibrations communicated along waveguide (148) and blade (152) in order to tune the acoustic assembly to a preferred resonant frequency $f_o$ when the acoustic assembly is not loaded by tissue. When transducer (126) is energized, the distal end of blade (152) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (152) may also vibrate in the y-axis at about 1 to about 10 percent of the motion in the x-axis. Of course, movement of blade (152) when transducer (126) is energized may alternatively have any other suitable characteristics.

Handle assembly (130) comprises a tubular elongate body (132) including a plurality of buttons (136). Elongate body (132) is configured to permit a user to grip handle assembly (130) from a variety of positions. By way of example only, handle assembly (130) may be shaped to be grasped and manipulated in a pencil-grip arrangement, in a screwdriver-grip arrangement, and/or in any other suitable fashion. Handle assembly (130) of the present example comprises mating housing portions (137) and (138), though it should be understood that handle assembly (130) may alternatively comprise just a single housing component. Housing portions (137, 138) may be constructed from a durable plastic, such as polycarbonate or a liquid crystal polymer. It is also contemplated that housing portions (137, 138) may alternatively be made from a variety of materials or combinations of materials, including but not limited to other plastics, ceramics, and/or metals, etc.

In the present example, body (132) of handle assembly (130) includes a proximal end, a distal end, and a cavity (not shown) extending longitudinally therein. The cavity is configured to accept a switch assembly (now shown), an actuation assembly (not shown), and at least a portion of ultrasonic transducer assembly (126), all in a manner similar to the teachings of U.S. patent application Ser. No. 14/515,129, entitled "Activation Features for Ultrasonic Surgical Instrument," filed Oct. 15, 2014, issued as U.S. Pat. No. 9,907,565 Mar. 6, 2018, the disclosure of which is incorporated by reference herein. In the present example, the distal end of transducer (126) threadably attaches to the proximal end of the waveguide, though any other suitable type of coupling may be used.

Electrical contacts of transducer (126) also interface with the switch assembly to provide the operator with finger-activated controls on surgical instrument (120). Transducer (126) of the present example includes two conductive rings (not shown) that are securely disposed within the body of transducer (126). By way of example only, such conductive rings and/or other features of transducer (126) may be provided in accordance with at least some of the teachings of U.S. Pat. No. 8,152,825, entitled "Medical Ultrasound System and Handpiece and Methods for Making and Tuning," issued Apr. 10, 2012, the disclosure of which is incorporated by reference herein.

The switch assembly provides an electro-mechanical interface between buttons (136) of handle assembly (130) and generator (12) via transducer (126) such that actuation of any of buttons (136) results in the activation of generator (12), which in turn activates transducer (126) to generate ultrasonic vibrations along waveguide (148) and blade (152). By way of example only, various components of switch assembly may interface with transducer (126) via ring conductors of transducer (126), which are in turn connected to conductors in cable (14) that connects to generator (12). Thus, when contact switch of switch assembly is actuated by the depressing of any of buttons (136), generator (12) activates transducer (126) to generate ultrasonic vibrations. Buttons (236) are provided in an annular array in this example, with buttons (236) being angularly spaced from each other equidistantly. Buttons (136) may be constructed and operable in accordance with at least some of the teachings of U.S. patent application Ser. No. 14/515,129, entitled "Activation Features for Ultrasonic Surgical Instrument," filed Oct. 15, 2014, issued as U.S. Pat. No. 9,907,565 on Mar. 6, 2018, the disclosure of which is incorporated by reference herein.

It should be understood that providing buttons (136) in an angular array may enable the operator to actuate one or more buttons (136) (and thereby activate transducer (126) and blade (152)) at various gripping positions about the longitudinal axis of handle assembly (130). In other words, the operator will not need to contort their fingers, hand, wrist, or arm in order to activate transducer (126) and blade (152) from whichever angular orientation the operator happens to be grasping handle assembly (130). This enhanced access to buttons (136) may be particularly useful when blade (152) has an asymmetry, such that engaging tissue with different sides of blade (152) (e.g., with blade (152) oriented at different angular orientations about the longitudinal axis of waveguide (148)) will provide different effects on tissue. The operator will thus not be forced to sacrifice ergonomic comfort in order to selectively achieve various orientations of blade (152) relative to tissue.

III. Exemplary Alternative Handle Assemblies with Circular Buttons

As noted above, there may be instances where it is desirable to enable an operator to engage tissue with an ultrasonic blade at various different angular orientations about the longitudinal axis of an ultrasonic waveguide that is coupled with the ultrasonic blade. This may be particularly desirable where the ultrasonic blade has an asymmetry, such the effect that the activated blade has on tissue will vary depending on the angular orientation (about the longitudinal axis of the waveguide) at which the blade engages tissue. It may therefore be desirable to enable the operator to continue to grasp and manipulate the handle assembly in the same way regardless of the angular orientation (about the longitudinal axis of the waveguide and the handle assembly) at which the handle assembly is positioned in the operator's hand. While buttons (136) provide one merely illustrative example of how this may be accomplished, it may be desirable to provide alternative components and configurations to accomplish a substantially similar goal. Various merely illustrative examples of such alternatives are described in greater detail below.

Some instances may also call for enabling activation of the transducer and blade at two or more ultrasonic power settings (e.g., where the amplitude, frequency, and/or other ultrasonic vibration parameters are varied). It may therefore be desirable to enable the operator to select among two or more ultrasonic power settings. Continuing with the premise of enhanced ergonomics, it may be further desirable to enable such power selection in the same way regardless of the angular orientation (about the longitudinal axis of the waveguide and the handle assembly) at which the handle assembly is positioned in the operator's hand. In other words, it may be desirable to enable the operator to select from different power settings or modes regardless of the angular orientation at which the operator happens to be grasping the handle assembly at that moment. The below discussion provides several merely illustrative examples of how such enhanced power mode selection may be provided.

While various alternative housing assemblies are described below as providing the above described features and functionality, it should be understood that other examples will be apparent to those of ordinary skill in the art in view of the teachings herein. It should be further understood that various features and/or structures of the housing assemblies described herein by be readily incorporated into other housing assemblies described herein.

Figure 3:
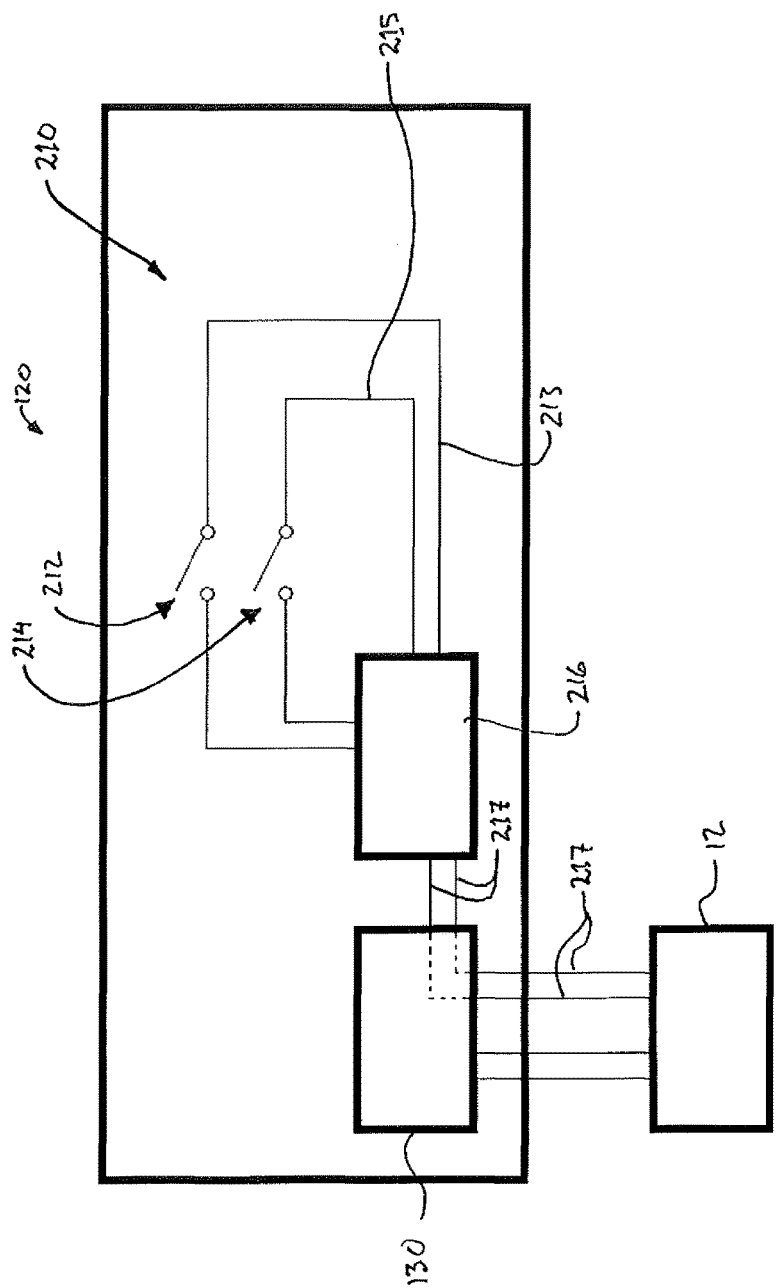
FIG. 3 depicts a block schematic view of an exemplary multi-button activation circuit that may be incorporated into the instrument of FIG. 2.

FIG. 3 schematically shows an exemplary circuit (210) that may be incorporated into instrument (120) described above and/or any other instruments (20) described herein. Generally, circuit (210) is configured to provide multiple operator inputs to permit an operator to activate blade (152) at varying ultrasonic power levels. Circuit (210) of the present example comprises two operator inputs in the form of switches (212, 214). Each switch (212, 214) corresponds to a high ultrasonic power level and a low ultrasonic power level for blade (152). However, in other examples circuit (210) includes any suitable number of operator inputs corresponding to any suitable number of ultrasonic power levels. Although switches (212, 214) are shown schematically, it should be understood that switches (212, 214) may take on any suitable form. For instance, as will be described in greater detail below, in one merely exemplary embodiment each switch (212, 214) comprises a circular ring disposed about a handle assembly that may be similar to handle assembly (130) described above. In other examples, switches (212, 214) may take on any suitable form as will be apparent to those of ordinary skill in the art in view of the teachings herein.

Each switch (212, 214) is in communication with a circuit board (216) via a respective wire loop (213, 215) corresponding to each switch (212, 214). Generally, circuit board (216) is configured to receive input signals from each switch (212, 214) and communicate such signals to other components of instrument (120). In the present example, circuit board (216) is in communication with handle assembly (130) of instrument (120) via a pair of wires (217). Wires (217) continue through handle assembly (130) to generator (12). Although circuit board (216) of the present example is shown as being in communication with both handle assembly (130) and generator (12), it should be understood that in other examples circuit board (216) is only in communication with generator (12). Indeed, in some examples circuit (210) is fully integrated into handle assembly (130) such that circuit board (216) communicates directly with generator (12) from handle assembly (130).

In the present example, circuit board (216) is configured for the processing of low voltage singles. In use, low voltage is used with switches (212, 214) to provide operator inputs. Circuit board (216) then relays the operator inputs to generator (12). Generator (12) is configured to receive such inputs and apply a predetermined voltage to handle assembly (130) via cable (14), which is shown as a plurality of wires. The particular predetermined voltage used may be any suitable voltage. Additionally, generator (12) may be configured to provide a plurality of predetermined voltages in repose to receiving a particular signal from circuit board (216). For instance, actuation of switch (212) may generate a first signal and actuation of switch (214) may generate a second signal. Upon receipt of the first signal, generator (12) may output a first predetermined voltage to handle assembly (130). Similarly, upon receipt of the second signal, generator (12) may output a second predetermined voltage to handle assembly (130). First and second voltages of the present example may correspond to a transducer supplying different ultrasonic power levels to blade (152).

While voltage is used to describe the electrical signal communicated from generator (12) to handle assembly (130) it should be understood that any other characteristic of the electronic signal (e.g., power, current, frequency, amplitude, etc.) may be changed in response to actuation of switches (212, 214). It should also be understood that circuit board (216) may take on any suitable form such as an analog or digital signal processing mechanism. Additionally, circuit board (216) may include any components suitable for processing electric signals between switches (212, 214) and generator (12). In other examples, circuit (210) may take on any other suitable form as will be apparent to those of ordinary skill in the art in view of the teachings herein.

A. Exemplary Alternative Handle Assembly with Central Electrical Contact

Figure 4:
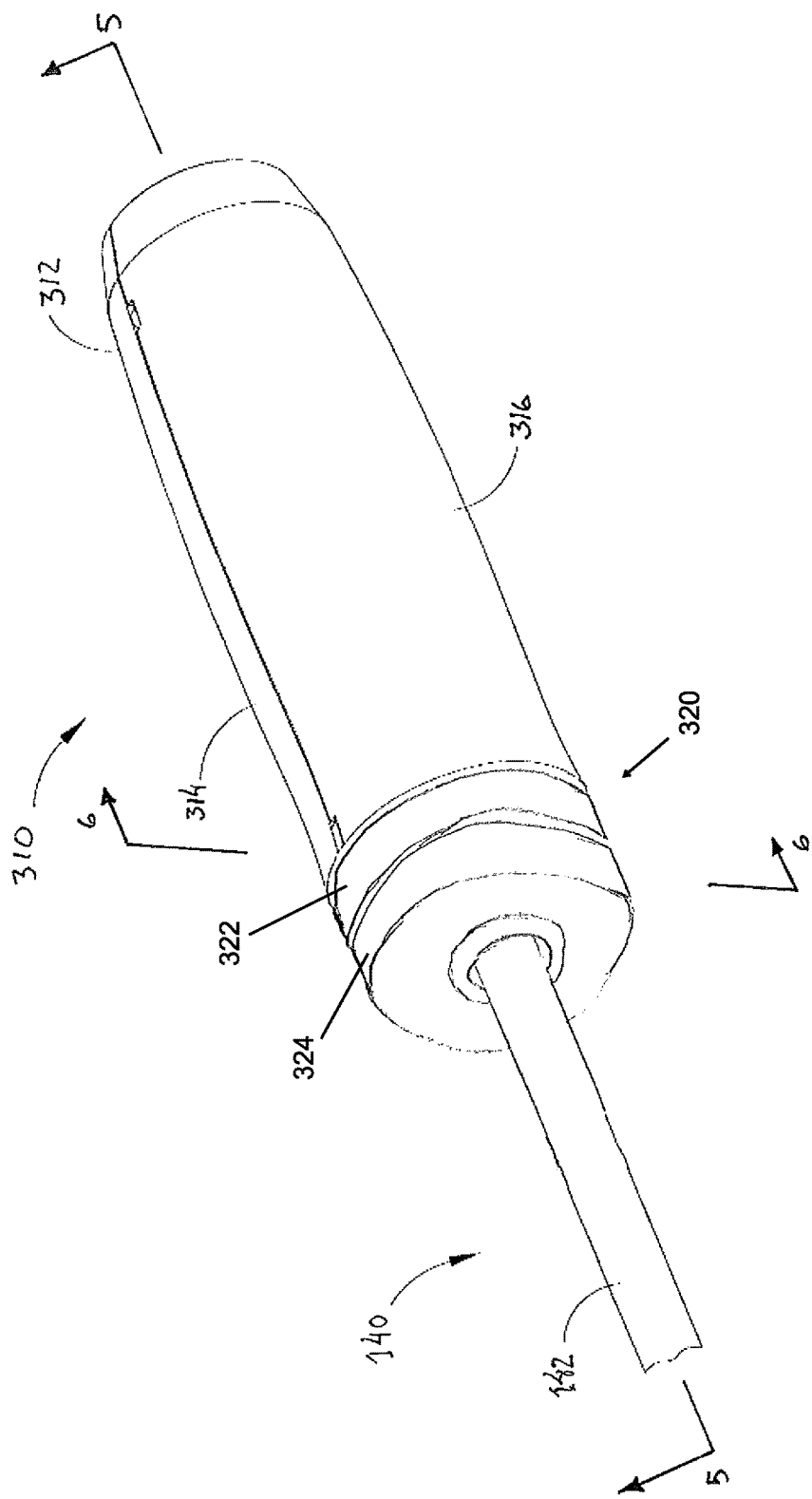
FIG. 4 depicts a perspective view of an exemplary alternative handle assembly that may be incorporated into the instrument of FIG. 2.

FIG. 4 shows an exemplary alternative handle assembly (310) that may be readily incorporated into ultrasonic instrument (120) described above. Handle assembly (310) is substantially the same as handle assembly (130) described above, unless otherwise described herein. For instance, handle assembly (310) comprises a tubular elongate body (312) defined by two mating housing portions (314, 316). Like with handle assembly (130), handle assembly (310) supports shaft assembly (140), which includes an outer sheath projecting from the distal end of handle assembly (310).

Unlike handle assembly (130), handle assembly (310) comprises a button assembly (320), which includes two discrete ring shaped buttons (322, 324) extending angularly around body (312) near the distal end of body (312). As will be described in greater detail below, each button (322, 324) is configured to be actuated radially inwardly from any angle around the perimeter of body (312), thereby laterally displacing the entire button (322, 324) relative to the central longitudinal axis of handle assembly (310), to activate blade (152) at one of two discrete power levels. Unlike buttons (136) described above, each button (322, 324) extends continuously about the perimeter of body (312). Moreover, each button (322, 324) has a discrete function in contrast to buttons (136), which all have an identical function. In the present example, each button (322, 324) is rigid such that button (322, 324) will not deform (but will move as a rigid unit) in response to an operator pressing radially inwardly against button (322, 324). In some other versions, at least a portion of each button (322, 324) may be deformable.

Figure 5:
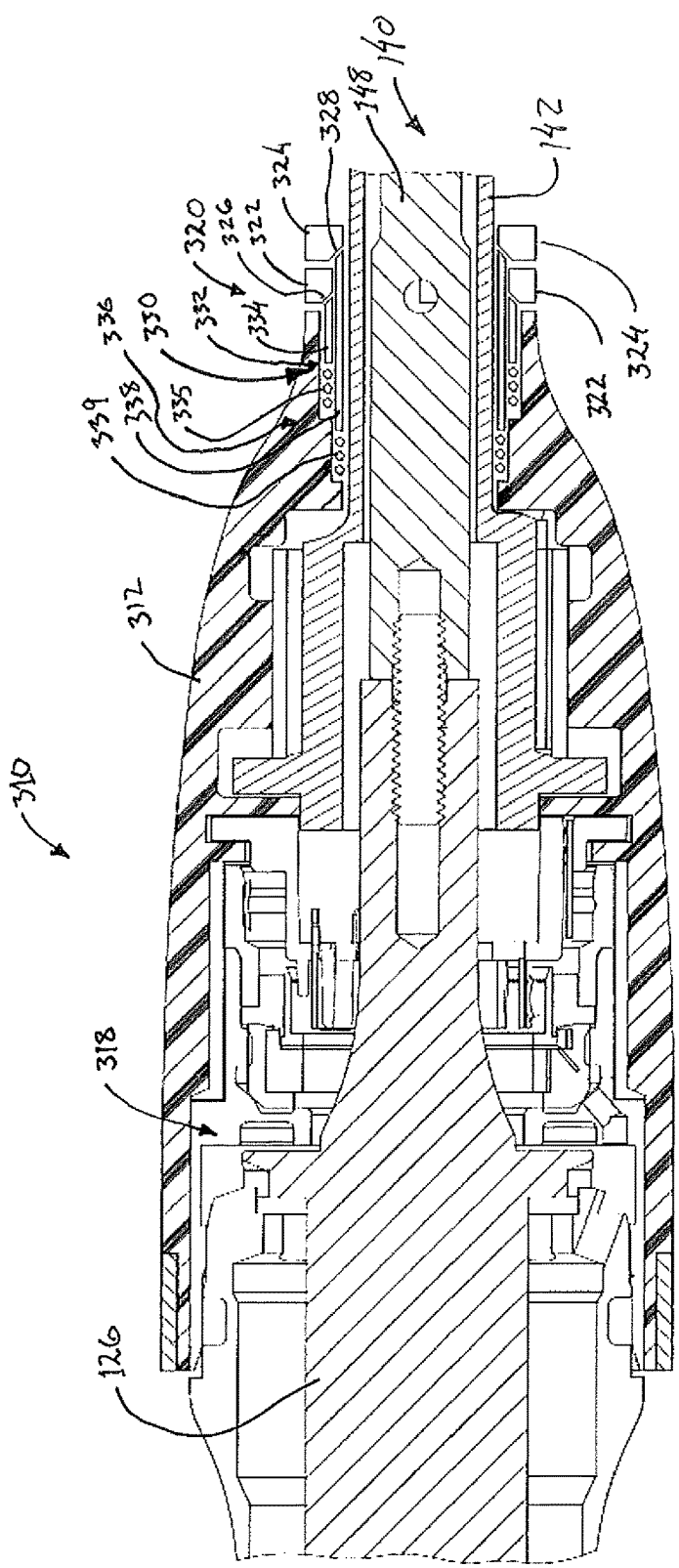
FIG. 5 depicts a side cross-sectional view of the handle assembly of FIG. 4, with the cross-section taken along line 5-5 of FIG. 4.

FIG. 5 shows the internal components of handle assembly (310). As can be seen, handle assembly (310) of the present example is equipped with an ultrasonic transducer (126), which is received within a cavity (318) defined by body (312). Transducer (126) is coupled to waveguide (148) of shaft assembly (140) such that transducer (126) may communicate ultrasonic vibrations to waveguide (148), thereby powering ultrasonic blade (152). By way of example only, suitable coupling features between transducer (126) and waveguide may be provided in accordance with at least some of the teachings of U.S. Ser. No. 14/515,129, entitled "Activation Features for Ultrasonic Surgical Instrument," filed Oct. 15, 2014, issued as U.S. Pat. No. 9,907,565 on Mar. 6, 2018; U.S. Pub. No. 2015/0148829, entitled "Methods and Features for Coupling Ultrasonic Surgical Instrument Components Together," published May 28, 2015, issued as U.S. Pat. No. 10,226,271 on Mar. 12, 2019; and U.S. Pat. No. 8,152,825, entitled "Medical Ultrasound System and Handpiece and Methods for Making and Tuning," issued Apr. 10, 2012, the disclosure of which is incorporated by reference herein.

Button assembly (320) is disposed coaxially about shaft assembly (140) at the distal end of body (312). Button assembly (320) comprises a proximal button (322), a distal button (324), and an alignment assembly (330). As described above, each button (322, 324) is generally ring shaped. The inside proximal diameter of each button (322, 324) includes a frustoconical cam feature (326, 328). As will be described in greater detail below, each cam feature (326, 328) is configured to engage with alignment assembly (330) to resiliently bias each button (322, 324) toward a position that is generally coaxial with shaft assembly (140).

Alignment assembly (330) comprises a separate alignment mechanism (332, 336) corresponding to each button (322, 324). Each alignment mechanism (332, 336) comprises a plurality of longitudinally translatable cam members (334, 338), which are resiliently biased distally by corresponding springs (335, 339). The distal end of each cam member (334, 338) is shaped to complement the frustoconical cam feature (326, 328) of the corresponding button (322, 324). Thus, as will be described in greater detail below, each cam member (334, 338) is configured to engage its corresponding button (322, 324) to resiliently bias the corresponding button (322, 324) toward a radial position of coaxial alignment with shaft assembly (140).

Figure 6:
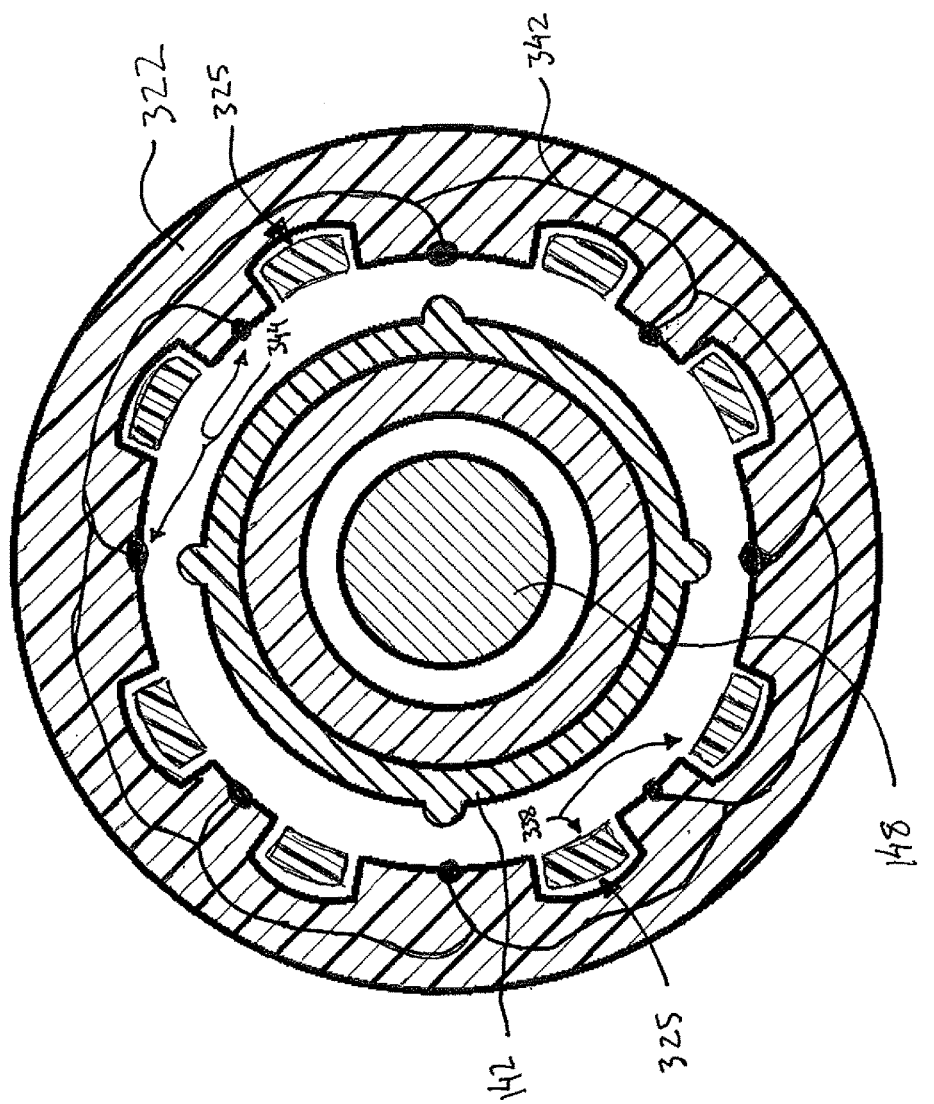
FIG. 6 depicts a front cross-sectional view of the handle assembly of FIG. 4, with the cross-section taken along line 6-6 of FIG. 4.

FIG. 6 shows a cross-section of button assembly (320) with the cross-section taken through proximal button (322). As can be seen, button (322) includes a plurality of inner channels (325) oriented around the inner diameter of button (322). Each channel (325) is configured to receive a single cam member (338), such that cam members (338) can pass through button (322) to button (324) without impacting movement of button (322). Thus, in the present example, cam members (338) comprise a plurality of discrete cam members (338) that work together to bias button (324). Although not explicitly shown, it should be understood that cam members (334) are similarly configured in the present example. While cam members (334, 338) are shown and described herein as comprising a plurality of discrete elements, it should be understood that no such limitation is intended. Indeed, in some examples each cam member (334, 338) may comprise a single discrete tubular element rather than a plurality of discrete elements. As will be described in greater detail below, some cam member (334, 338) configurations may be more or less desirable depending on the particular configuration of buttons (322, 324).

While not shown, it should also be understood that handle assembly (310) may include guide features that are configured to permit each cam member (334, 338) to translate longitudinally; yet prevent each cam member (334, 338) from deflecting laterally relative to the longitudinal axis of shaft assembly (140). Such guide features may comprise one or more channels and bosses formed in body (312), one or more chassis components that are coupled with body (312), and/or any other suitable components or configurations. Various suitable components and configurations that may be used to guide each cam member (334, 338) will be apparent to those of ordinary skill in the art in view of the teachings herein.

As shown in FIG. 6, button (322) includes a wire (342) disposed therein. Wire (342) is coupled to a plurality of discrete electrically conductive contacts (344), which are disposed about the inner diameter of button (322). Although not shown, it should be understood that wire (342) is connected to a circuit board similar to circuit board (216) described above. As will be described in greater detail below, such a connection is configured to permit button (322) to complete an activation circuit, which activates blade (152) at a particular ultrasonic power level.

Conductive contacts (344) of the present example are spaced evenly about the inner diameter of proximal button (322). As will be understood, the positioning of contacts (344) permits proximal button (322) to make electrical contact with outer sheath (142) of shaft assembly (140) when proximal button (322) is moved radially inwardly toward outer sheath (142) from a variety of angular positions about the longitudinal axis of shaft assembly (140). Although the present example is shown as having a plurality of contacts (344), it should be understood that in other examples contact (344) may take on other forms or configurations. For instance, in one alternative example proximal button (322) includes a single electrical contact comprising an electrically conductive trace extending around the inner diameter of proximal button (322). In other examples, proximal button (322) may include any other suitable conductive contact (344) positioning as will be apparent to those of ordinary skill in the art in view of the teachings herein.

Although not shown, it should be understood that button (324) includes conductive contacts similar to conductive contacts (344) described above with respect to button (322). Similarly, button (324) is also equipped with a wire that is similar to wire (342) described above. However, unlike wire (342), the wire of button (324) is configured to complete a separate activation circuit when the conductive contacts of button (324) are brought into contact with outer sheath (142). As will be described in greater detail below, this permits distal button (324) to activate blade (152) at a different level of power than the level of power activated by proximal button (322).

As described above, each button (322, 324) is associated with a corresponding activation circuit. In the present example, the opposite lead of each activation circuit is in communication with outer sheath (142). As can be seen in FIG. 6, the portion of outer sheath (142) positioned interior to buttons (322, 324) comprises a conductive metallic material. Because of the conductive properties of this region of outer sheath (142), when either button (322, 324) is moved into contact with outer sheath (142), the corresponding activation circuit is completed as an electrical signal is communicated through outer sheath (142). Thus, outer sheath (142) of the present example acts as an electrical conductor to complete either activation circuit associated with each button (322, 324).

In some examples, it may be desirable for outer sheath (142) to be non-conductive or otherwise not be configured to carry an electrical charge. Thus, in some examples outer sheath (142) includes an electrical trace printed or otherwise disposed on the outer diameter of outer sheath (142). In examples utilizing such an electrical trace, the electrical trace may include rings around outer sheath at a longitudinal position along outer sheath (142) corresponding to conductive contacts (344) of proximal button (322) and the conductive contacts of distal button (324). Alternatively, in some examples, two traces may be used with one trace corresponding to each button (322, 324), rather than a single common trace for each button (322, 324). In still other examples, outer sheath (142) may be equipped with wires and conductors as similarly described above with respect to proximal button (322).

Figure 7:
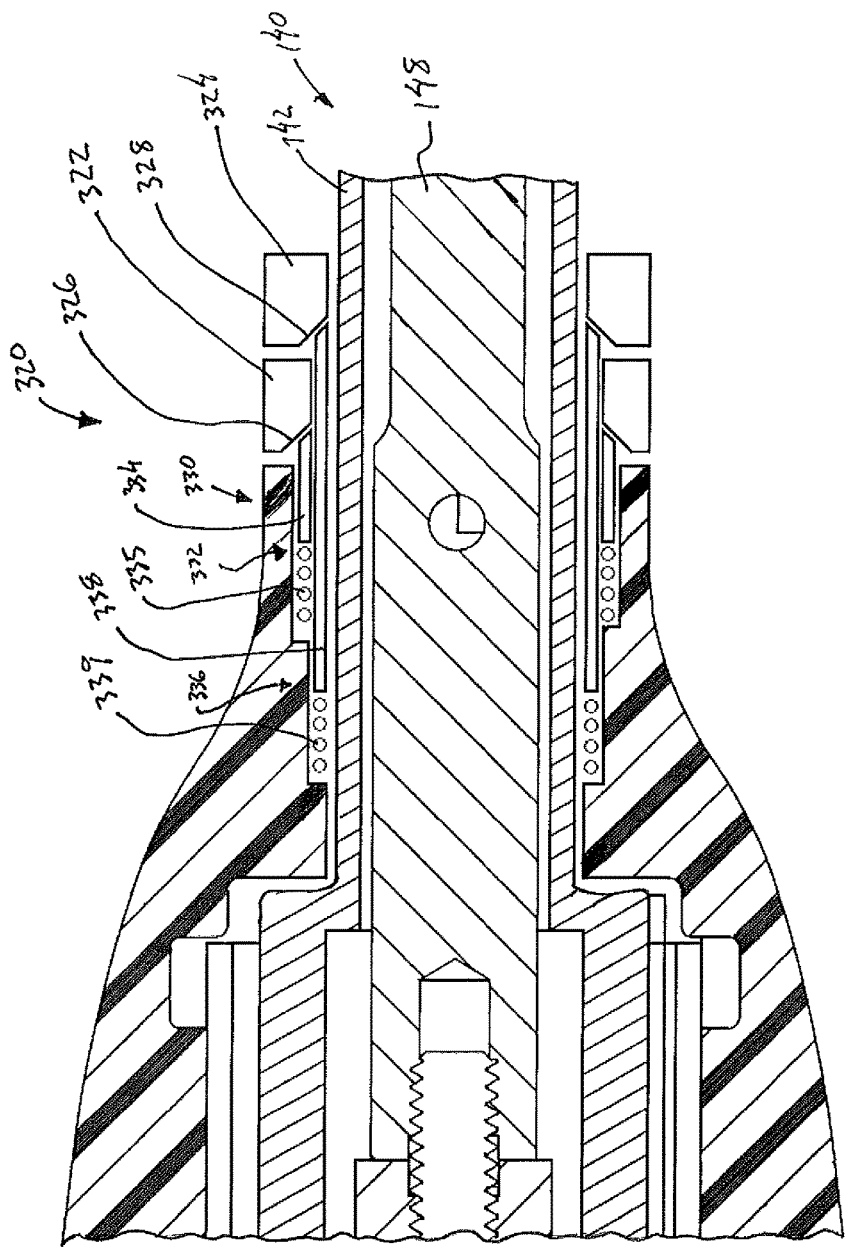
FIG. 7 depicts another side cross-sectional view of the handle assembly of FIG. 4, with a pair of activation rings in an unactivated position.
Figure 8:
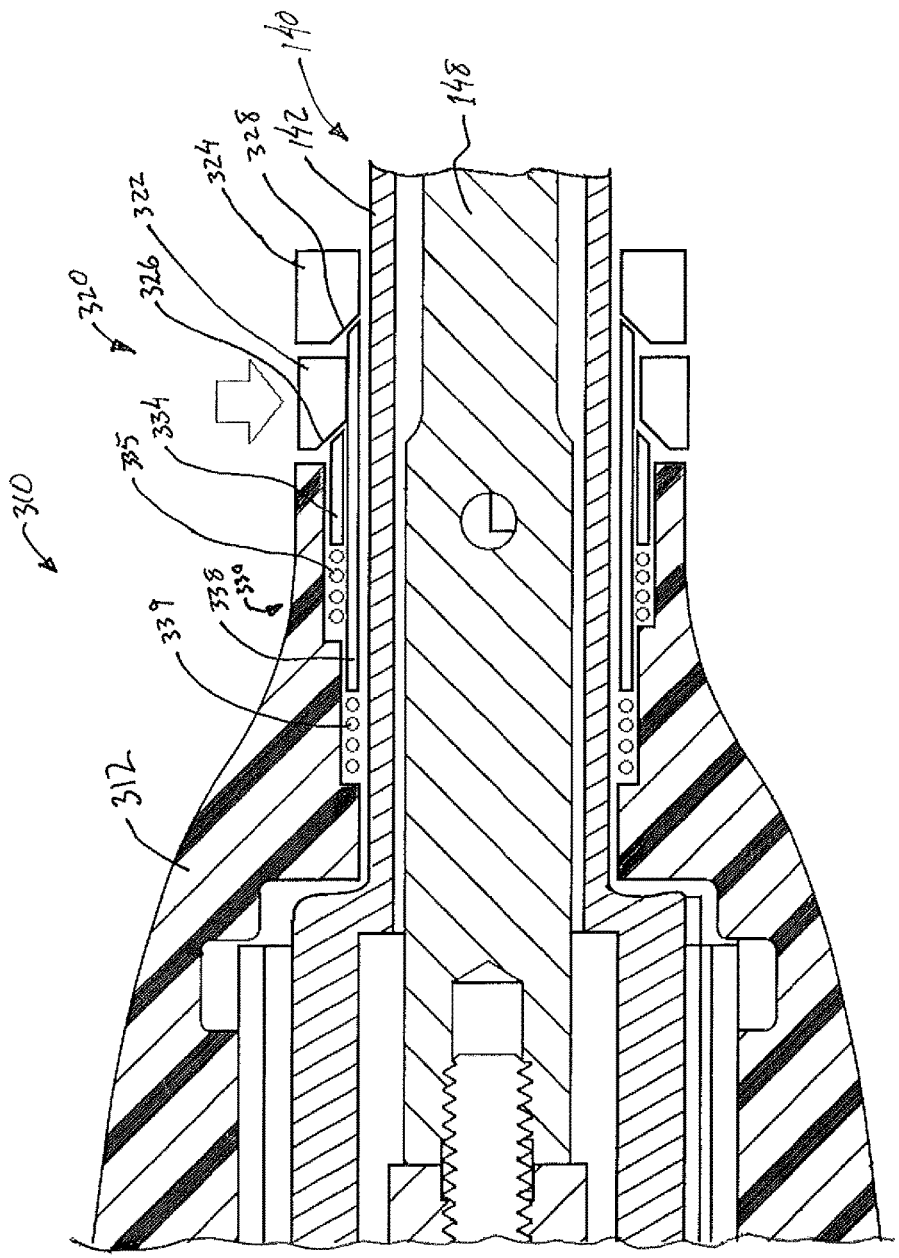
FIG. 8 depicts still another side cross-sectional view of the handle assembly of FIG. 4, with a first activation ring in an activated position.
Figure 9:
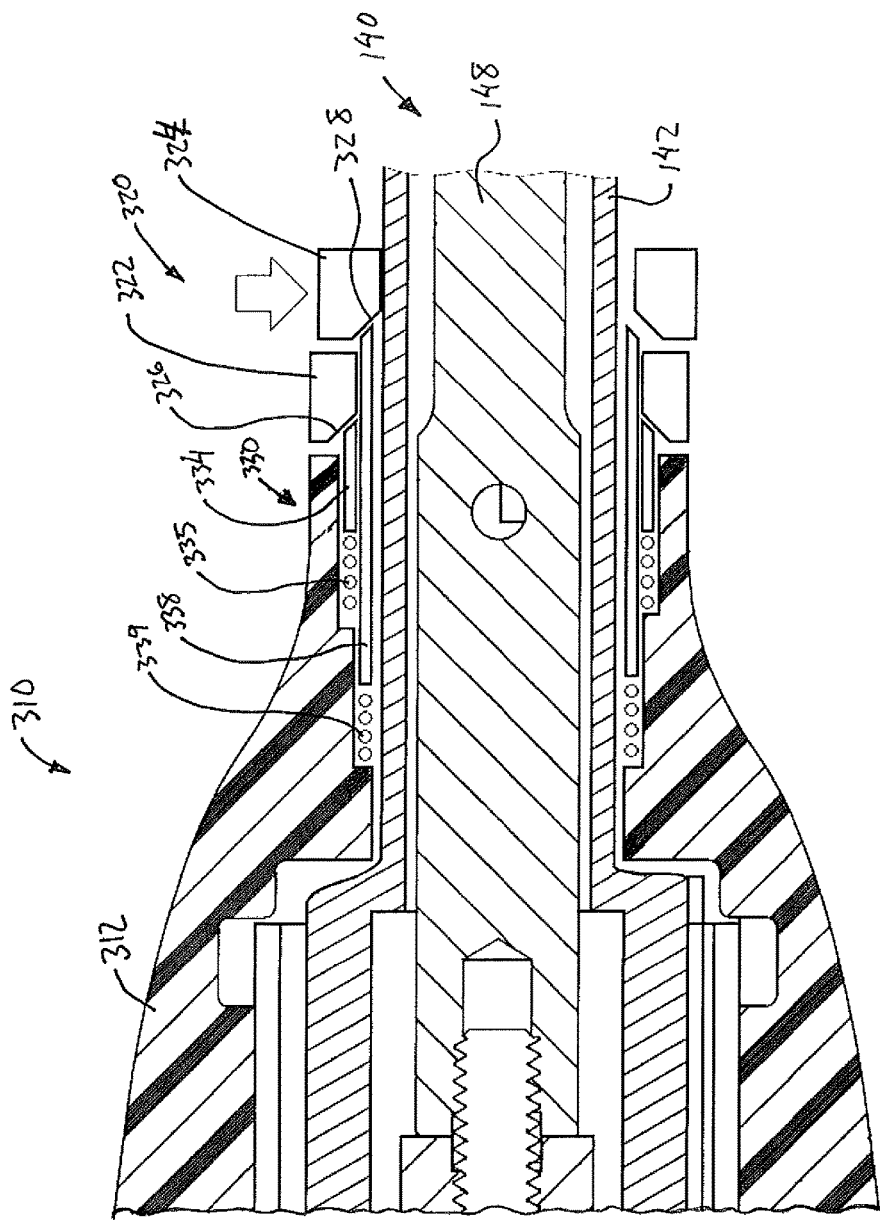
FIG. 9 depicts yet another side cross-sectional view of the handle assembly of FIG. 4, with a second activation ring in an activated position.

FIGS. 7-9 depict an exemplary use of handle assembly (310) to activate blade (152) with ultrasonic energy and varying degrees of power. As can be seen in FIG. 7, buttons (322, 324) of button assembly (320) initially begin in a neutral position. In the neutral position, each alignment mechanism (332, 336) of alignment assembly (330) generally acts on each corresponding button (322, 324) to laterally position each button (322, 324) such that each button (322, 324) is coaxially aligned with shaft assembly (140). In particular, each cam member (334, 338) is resiliently biased distally by each cam member's (334, 338) respective spring (335, 339). The distal end of each cam member (334, 338) in turn acts on cam feature (326, 328) of each respective button (322, 324). This engagement between cam members (334, 338) and cam features (326, 328) generates an outwardly oriented force on buttons (322, 324). This outwardly oriented force is uniform about the entire circumference of each cam member (334, 338). Thus, because cam members (334, 338) extend along a full circle within the inner diameter associated with button (322, 324), the net force resiliently biases each button (322, 324) laterally toward a position that is coaxial with the central longitudinal axis of shaft assembly (140).

When both buttons (322, 324) are in the neutral position, there is no contact between either button (322, 324) and shaft assembly (140). The activation circuits associated with buttons (322, 324) are therefore both in an open circuit state. When each activation circuit is in the open circuit state, blade (152) is inactive and not ultrasonically energized.

To activate blade (152) via proximal button (322), an operator may push proximal button (322) toward the central longitudinal axis of shaft assembly (140). As can be seen in FIG. 8, the force is shown as being applied to an upper portion of proximal button (322). However, it should be understood that an operator may apply a similar force at any point around the outer diameter of proximal button (322) to achieve the same result of activating blade (152) at the power level associated with proximal button (322).

As proximal button (322) is pressed by an operator, proximal button (322) moves laterally relative to body (312) of handle assembly (310) such that proximal button (322) is displaced from the initial coaxial alignment with shaft assembly (140). The force applied by an operator is sufficient to overcome the resilient bias supplied by spring (335). Thus, as proximal button (322) is displaced laterally, cam member (334) is driven proximally by the frustoconical shape of cam feature (326).

Continued lateral displacement of proximal button (322) will eventually result in physical contact between at least a portion of the inner diameter of proximal button (322) and the outer diameter of outer sheath (142) of shaft assembly (140). Because of channels (325) in proximal button (322), movement toward shaft assembly (140) is not impeded by cam members (338) associated with distal button (324). Once contact is made between proximal button (322) and outer sheath (142) of shaft assembly (140), electrical contact is made between contacts (344) of proximal button (322) and outer sheath (142). With such electrical contact, the activation circuit associated with proximal button (322) is completed and thereby transitioned to a closed circuit state. With the circuit associated with proximal button (322) in a closed circuit state, blade (152) is activated at a first predetermined power level. In some versions, this first power level is a relatively low power level.

It should be understood that activation of blade (152) may be accomplished as similarly described above with respect to circuit (210). For example, the activation circuit associated with proximal button (322) may be a low voltage circuit in communication with a circuit board, similar to circuit board (216), which may in turn be in communication with to a generator that powers blade (152) via transducer (126) via waveguide (148).

Once an operator desires to deactivate blade (152) from the power level associated with proximal button (322), the operator may release proximal button (322). Alignment assembly (330) may then return proximal button (322) to the neutral position as described above with respect to FIG. 7.

To activate blade (152) via distal button (324), an operator may push distal button (324) toward the central longitudinal axis of shaft assembly (140). As can be seen in FIG. 9, the force is shown as being applied to an upper portion of distal button (324). However, it should be understood that an operator may apply a similar force at any point around the outer diameter of distal button (324) to achieve the same result of activating blade (152) at the power level associated with distal button (324).

As distal button (324) is pressed by an operator, distal button (324) moves laterally relative to body (312) of handle assembly (310) such that distal button (324) is displaced from the initial coaxial alignment with shaft assembly (140). The force applied by an operator is sufficient to overcome the resilient bias supplied by spring (339). Thus, as distal button (324) is displaced laterally, cam member (338) is driven proximally by the frustoconical shape of cam feature (328).

Continued displacement of distal button (324) will eventually result in physical contact between at least a portion of the inner diameter of distal button (324) and the outer diameter of outer sheath (142) of shaft assembly (140). Once contact is made between distal button (324) and outer sheath (142) of shaft assembly (140), electrical contact is made between the contacts of distal button (324) and outer sheath (142). With such electrical contact, the activation circuit associated with distal button (324) is completed and thereby transitioned to a closed circuit state. With the circuit associated with distal button (324) in a closed circuit state, blade (152) is activated at a second predetermined power level. In some versions, this second power level is a relatively high power level.

It should be understood that activation of blade (152) may be accomplished as similarly described above with respect to circuit (210). For example, the activation circuit associated with distal button (324) may be a low voltage circuit in communication with a circuit board, similar to circuit board (216), which may in turn be in communication with to a generator that powers blade (152) via transducer (126) via waveguide (148).

Once an operator desires to switch power levels, or otherwise deactivate blade (152) at the power level associated with distal button (324), the operator may release distal button (324). Alignment assembly (330) may then return distal button (324) to the neutral position as described above with respect to FIG. 7.

B. Exemplary Alternative Handle Assembly with Discrete Electrical Contacts

Figure 10:
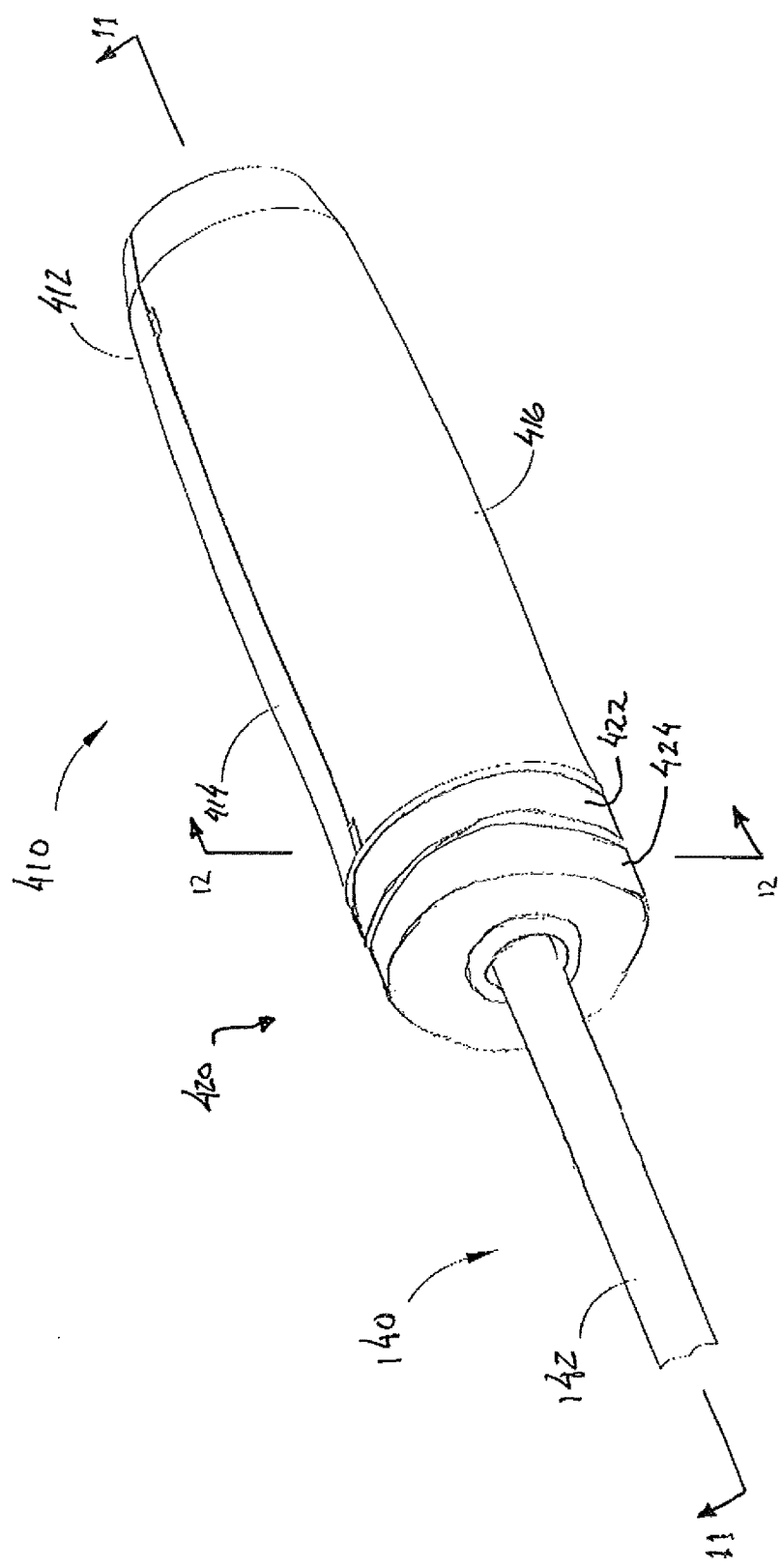
FIG. 10 depicts a perspective view of another exemplary alternative handle assembly that may be incorporated into the instrument of FIG. 2.

FIG. 10 shows another exemplary alternative handle assembly (410) that may be readily incorporated into ultrasonic instrument (120) described above. Handle assembly (410) is substantially the same as handle assembly (130) described above, unless otherwise described herein. For instance, handle assembly (410) comprises a tubular elongate body (412) defined by two mating housing portions (414, 416). Like with handle assembly (130), handle assembly (410) supports shaft assembly (140), which includes an outer sheath projecting from the distal end of handle assembly (410).

Unlike handle assembly (130), handle assembly (410) comprises a button assembly (420), which includes two discrete ring shaped buttons (422, 424) extending angularly around body (412) near the distal end of body (412). As will be described in greater detail below, each button (422, 424) is configured to be actuated radially inwardly from any angle around the perimeter of body (412), thereby laterally displacing the entire button (422, 424) relative to the central longitudinal axis of handle assembly (410), to activate blade (152) at one of two discrete power levels. Unlike buttons (136) described above, each button (422, 424) is continuous about the perimeter of body (412). Moreover, each button (422, 424) has a discrete function in contrast to buttons (136), which have an identical function. In the present example, each button (422, 424) is rigid such that button (422, 424) will not deform (but will move as a rigid unit) in response to an operator pressing radially inwardly against button (422, 424). In some other versions, at least a portion of each button (422, 424) may be deformable.

Figure 11:
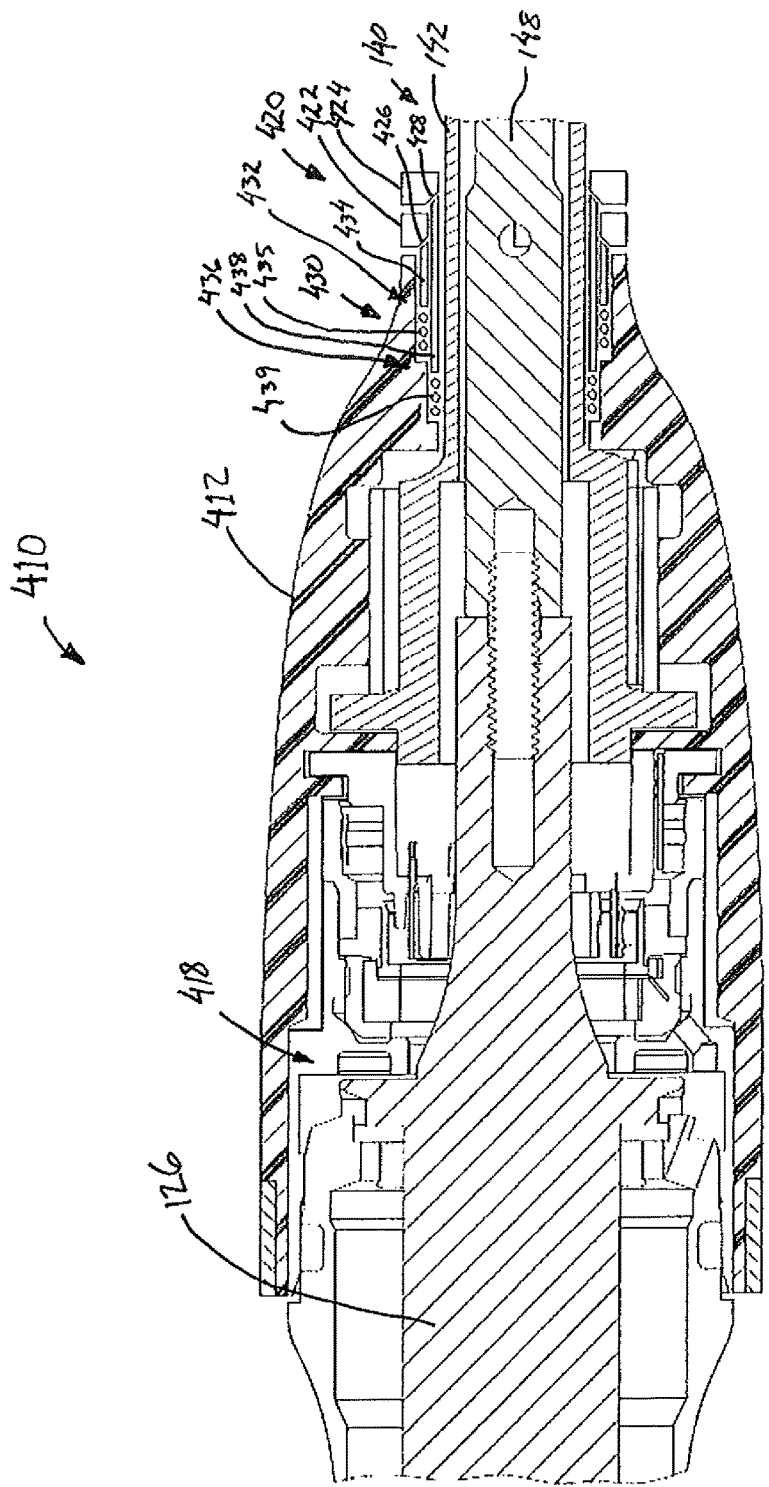
FIG. 11 depicts a side cross-sectional view of the handle assembly of FIG. 10, with the cross-section taken along line 11-11 of FIG. 10.

FIG. 11 shows the internal components of handle assembly (410). As can be seen, handle assembly (410) of the present example is equipped with an ultrasonic transducer (126), which is received within a cavity (418) defined by body (412). Transducer (126) is coupled to waveguide (148) of shaft assembly (140) such that transducer (126) may communicate ultrasonic vibrations to waveguide (148), thereby powering ultrasonic blade (152). By way of example only, suitable coupling features between transducer (126) and waveguide may be provided in accordance with at least some of the teachings of U.S. Ser. No. 14/515,129, entitled "Activation Features for Ultrasonic Surgical Instrument," filed Oct. 15, 2014, issued as U.S. Pat. No. 9,907,565 on Mar. 6, 2018; U.S. Pub. No. 2015/0148829, entitled "Methods and Features for Coupling Ultrasonic Surgical Instrument Components Together," published May 28, 2015, issued as U.S. Pat. No. 10,226,271 on Mar. 12, 2019; and U.S. Pat. No. 8,152,825, entitled "Medical Ultrasound System and Handpiece and Methods for Making and Tuning," issued Apr. 10, 2012, the disclosure of which is incorporated by reference herein.

Button assembly (420) is disposed coaxially about shaft assembly (140) at the distal end of body (412). Button assembly (420) comprises a proximal button (422), a distal button (424), and an alignment assembly (430). As described above, each button (422, 424) is generally ring shaped. The inside proximal diameter of each button (422, 424) includes a frustoconical cam feature (426, 428). As will be described in greater detail below, each cam feature (426, 428) is configured to engage with alignment assembly (430) to resiliently bias each button (422, 424) toward a position that is generally coaxial with shaft assembly (140).

Alignment assembly (430) comprises a separate alignment mechanism (432, 436) corresponding to each button (422, 424). Each alignment mechanism (432, 436) comprises a plurality of longitudinally translatable cam members (434, 438), which are resiliently biased distally by corresponding springs (435, 439). The distal end of each cam member (434, 438) is shaped to correspond to the frustoconical cam feature (426, 428) of the corresponding button (422, 424). Thus, as will be described in greater detail below, each cam member (434, 438) is configured to engage its corresponding button (422, 424) to resiliently bias the corresponding button (422, 424) toward a radial position of coaxial alignment with shaft assembly (140).

Figure 12:
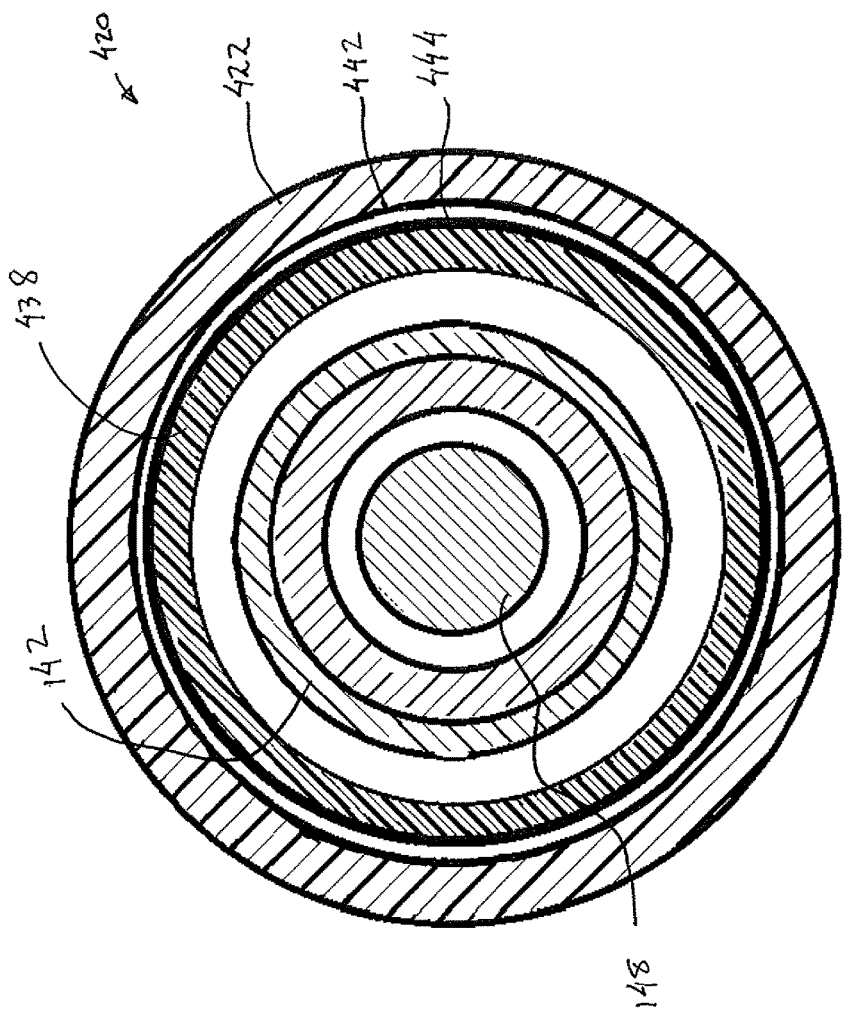
FIG. 12 depicts a front cross-sectional view of the handle assembly of FIG. 10, with the cross-section taken along line 12-12 of FIG. 10.

FIG. 12 shows a cross-section of button assembly (420) with the cross-section taken through proximal button (422). Unlike proximal button (322) of handle assembly (310) described above, proximal button (422) of the present example omits inner channels (325). Instead, proximal button (422) includes a substantially solid inner diameter that is configured to directly contact the cam member (438) that is associated with distal button (424), as will be described in greater detail below. Similarly, cam member (438) of the present example comprises a single tubular member, rather than a plurality of discrete members. Although not explicitly shown, it should be understood that cam member (434) is similarly configured in the present example. While cam members (434, 438) are shown and described herein as comprising a single tubular element, it should be understood that no such limitation is intended. Indeed, in some examples each cam member (434, 438) may instead comprise a plurality of discrete elements, much like cam members (334, 338) described above.

As can also be seen in FIG. 12, proximal button (422) includes a conductive coating (442) adhered or otherwise secured to the inner diameter of proximal button (422). Coating (442) comprises a thin film of electrically conductive material that extends around the entire inner diameter of proximal button (422). Although not shown, it should be understood that coating (442) is connected to one or more wires or traces that are in communication with a circuit board similar to circuit board (216) described above. Cam member (438) similarly includes a conductive coating (444). As will be described in greater detail below, such a connection is configured to permit proximal button (422) to complete an activation circuit when brought into contact with cam member (438), which activates blade (152) at a particular ultrasonic power level.

Although not shown, it should be understood that distal button (424) includes conductive coating similar to coating (442) described above with respect to proximal button (422). Similarly, distal button (424) is also equipped with a wire that is similar to the wire or trace associated with proximal button (422) described above. However, unlike the wire associated with proximal button (422), the wire of distal button (424) is configured to complete a separate activation circuit when the coating of distal button (424) is brought into contact with outer sheath (142). As will be described in greater detail below, this permits distal button (424) to activate blade (152) at a different level of power than the level of power activated by proximal button (422).

As described above, each button (422, 424) is associated with a corresponding activation circuit. In the present example, the opposite lead of each activation circuit is in communication with conductive coating (444) of cam member (438) or outer sheath (142). In particular, for the activation circuit associated with proximal button (422), the opposite lead is in communication with conductive coating (444) of cam member (438). Correspondingly, the activation circuit associated with distal button (424) is in communication with outer sheath (142). As can be seen in FIG. 12, outer sheath (142) comprises a conductive metallic material. Because of the conductive properties of outer sheath (142), when distal button (424) is moved into contact with outer sheath (142) the corresponding activation circuit is completed as an electrical signal is communicated through outer sheath (142). Thus, outer sheath (142) of the present example acts as an electrical conductor to complete the activation circuit associated with distal button (424).

In some examples, it may be desirable for outer sheath (142) to be non-conductive or otherwise not be configured to carry an electrical charge. Thus, in some examples outer sheath (142) includes an electrical trace printed or otherwise disposed on the outer diameter of outer sheath (142). In examples utilizing such an electrical trace, the electrical trace may include rings around outer sheath at a longitudinal position along outer sheath (142) corresponding to the conductive coating of distal button (424). In other examples, outer sheath (142) may be equipped with wires and conductors as described above with respect to proximal button (322) of handle assembly (310).

Figure 13:
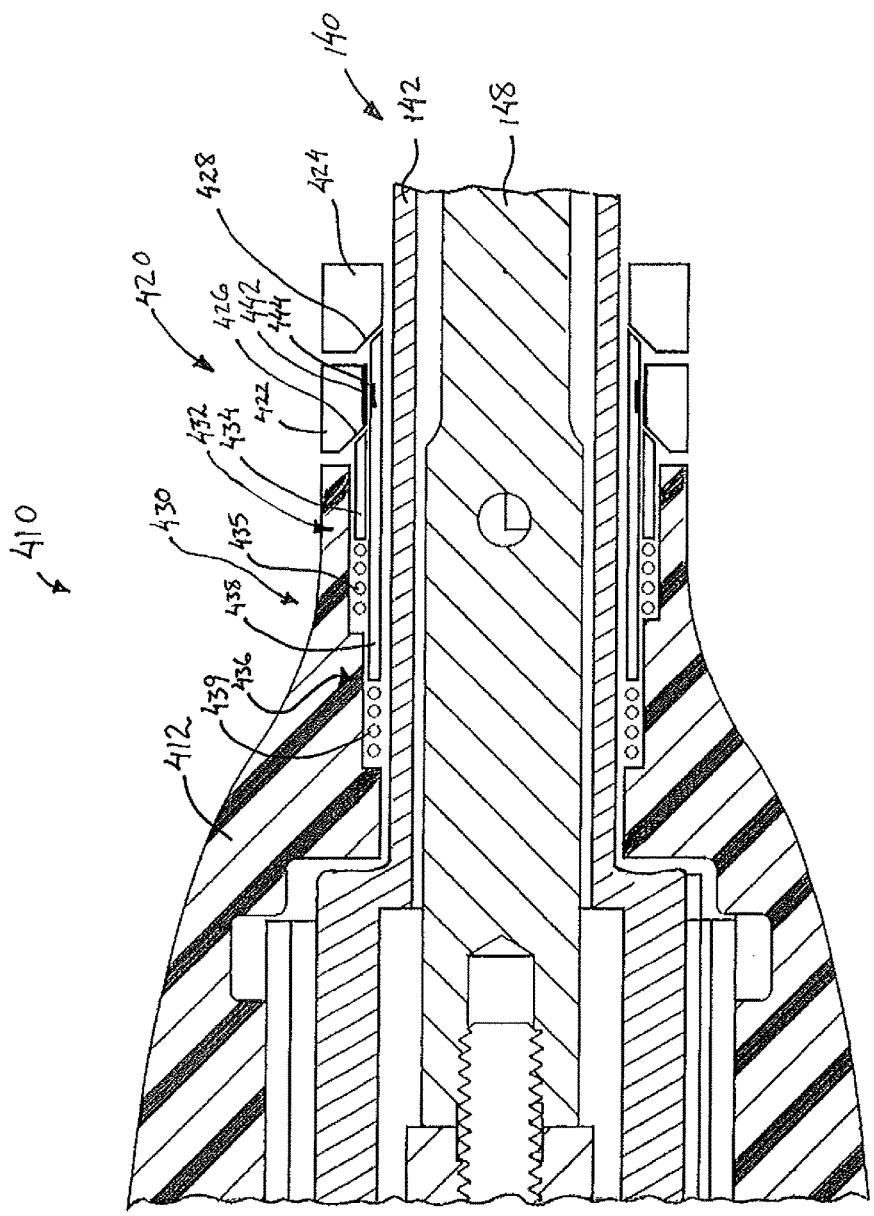
FIG. 13 depicts another side cross-sectional view of the handle assembly of FIG. 10, with a pair of activation rings in a neutral position.
Figure 14:
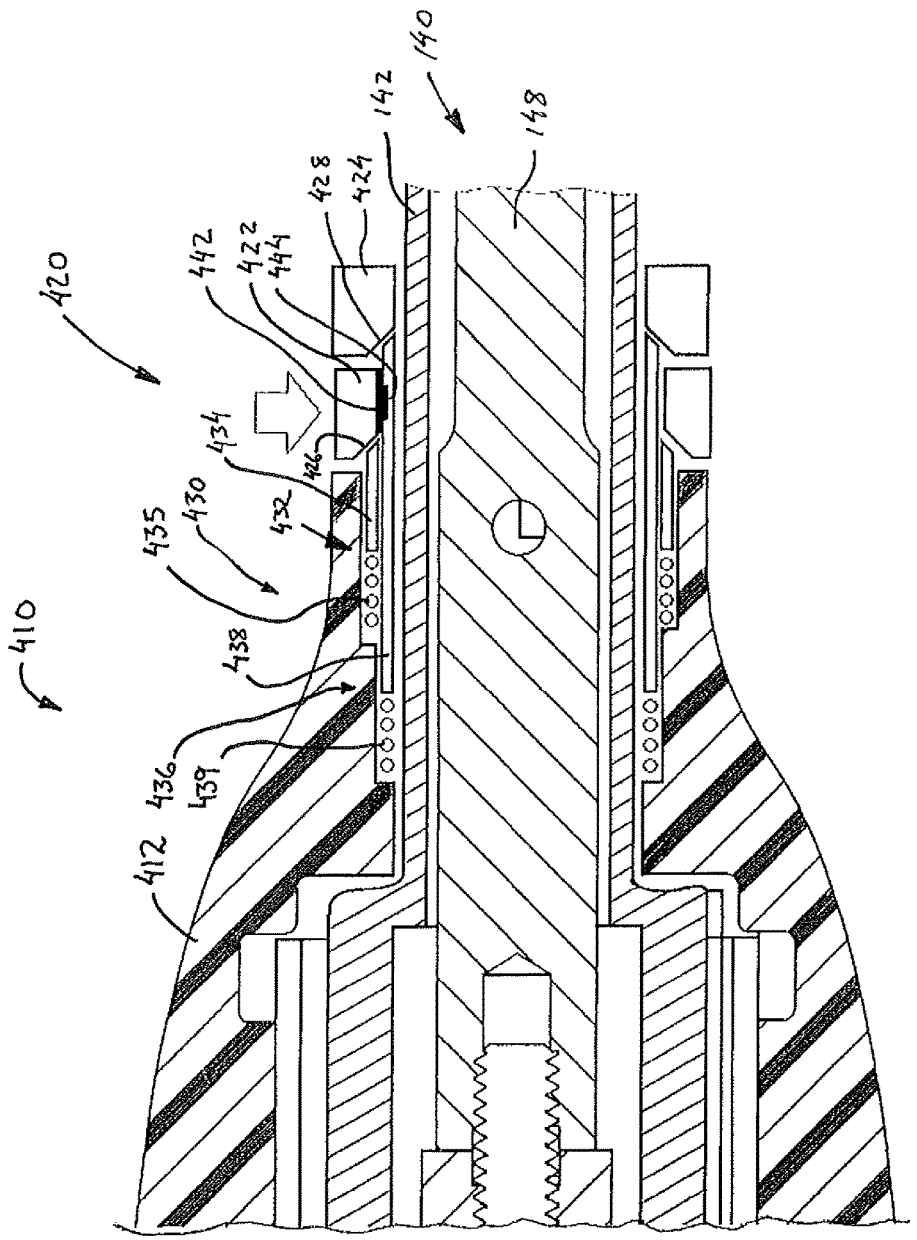
FIG. 14 depicts still another side cross-sectional view of the handle assembly of FIG. 10, with a first activation ring in an activated position.
Figure 15:
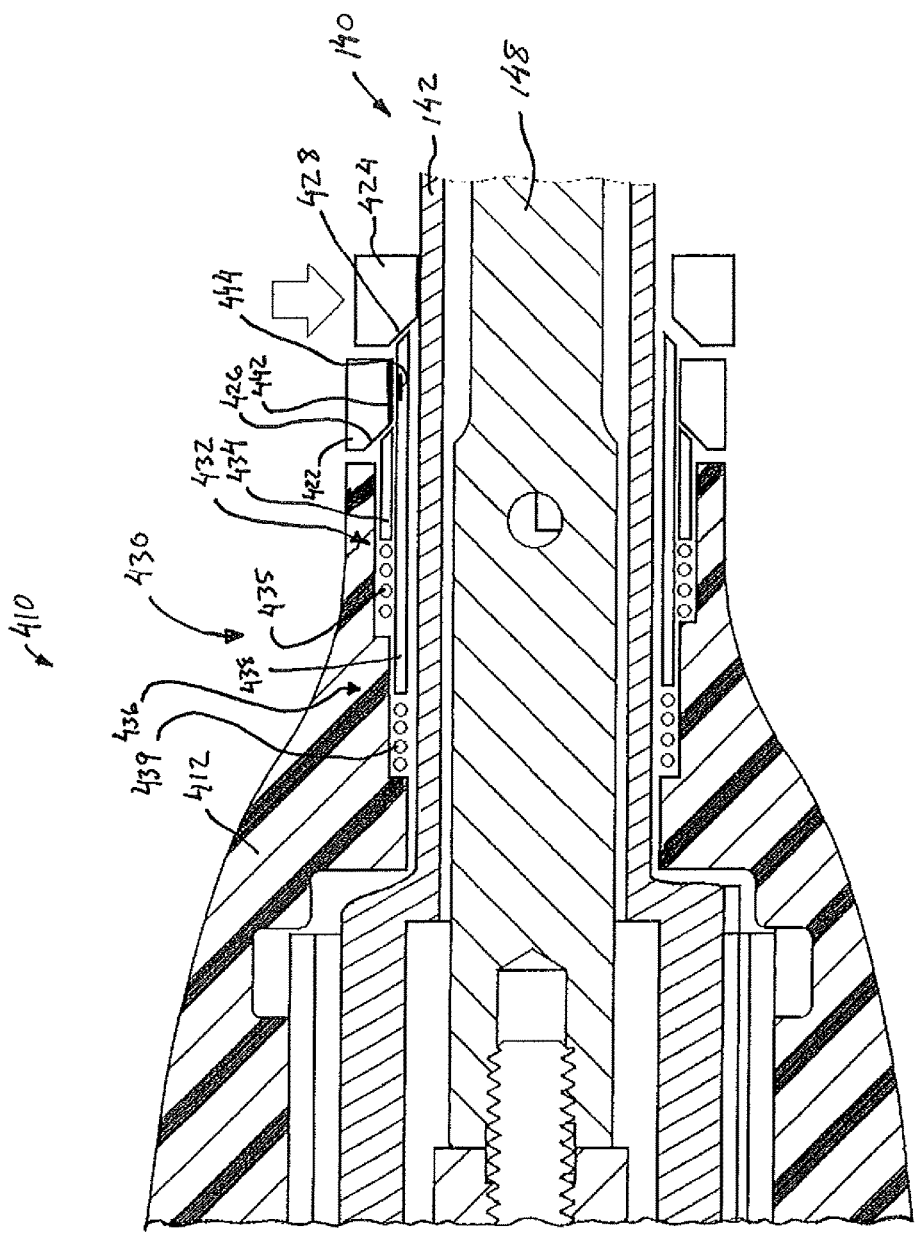
FIG. 15 depicts yet another side cross-sectional view of the handle assembly of FIG. 10, with a second activation ring in an activated position.

FIGS. 13-15 depict an exemplary use of handle assembly (410) to activate blade (152) with ultrasonic energy and varying degrees of power. As can be seen in FIG. 13, buttons (422, 424) of button assembly (420) initially begin in a neutral position. In the neutral position, each alignment mechanism (432, 436) of alignment assembly (430) generally acts on each corresponding button (422, 424) to laterally position each button (422, 424) such that each button (422, 424) is coaxially aligned with shaft assembly (140). In particular, each cam member (434, 438) is resiliently biased distally by each cam member's (434, 438) respective spring (435, 439). The distal end of each cam member (434, 438) in turn acts on cam feature (426, 428) of each respective button (422, 424). This engagement between cam members (434, 438) and cam features (426, 428) generates an outwardly oriented force on buttons (422, 424). This outwardly oriented force is uniform about the entire circumference of each cam member (434, 438). Thus, because cam members (434, 438) extend along a full circle within the inner diameter associated with button (422, 424), the net force resiliently biases each button (422, 424) laterally toward a position that is coaxial with the central longitudinal axis of shaft assembly (140).

When proximal button (422) is in the neutral position, there is no contact between proximal button (422) and cam member (438). Likewise, when distal button (424) is in the neutral position, there is no contact between distal button (424) and shaft assembly (140). Thus the activation circuits associated with buttons (422, 424) are in an open circuit state. When each activation circuit is in the open circuit state, blade (152) is inactive and not ultrasonically energized.

To activate blade (152) via proximal button (422), an operator may push proximal button (422) toward the central longitudinal axis of shaft assembly (140). As can be seen in FIG. 14, the force is shown as being applied to an upper portion of proximal button (422). However, it should be understood that an operator may apply a similar force at any point around the outer diameter of proximal button (422) to achieve the same result of activating blade (152) at the power level associated with proximal button (422).

As proximal button (422) is pressed by an operator, proximal button (422) moves laterally relative to body (412) of handle assembly (410) such that proximal button (422) is displaced from the initial coaxial alignment with shaft assembly (140). The force applied by an operator is sufficient to overcome the resilient bias supplied by spring (435). Thus, as proximal button (422) is displaced laterally, cam member (434) is driven proximally by the frustoconical shape of cam feature (426).

Continued lateral displacement of proximal button (422) will eventually result in physical contact between at least a portion of coating (442) of the inner diameter of proximal button (422) and coating (444) of the outer diameter of cam member (438). Once contact is made between coating (442) of proximal button (322) and coating (444) of cam member (438), electrical contact is made. With such electrical contact, the activation circuit associated with proximal button (422) is completed and thereby transitioned to a closed circuit state. With the activation circuit associated with proximal button (422) in a closed circuit state, blade (152) is activated at a first predetermined power level. In some versions, this first power level is a relatively low power level.

It should be understood that activation of blade (152) may be accomplished as similarly described above with respect to circuit (210). For example, the activation circuit associated with proximal button (422) may be a low voltage circuit in communication with a circuit board, similar to circuit board (216), which may in turn be in communication with to a generator that powers blade (152) via transducer (126) via waveguide (148).

Once an operator desires to deactivate blade (152) from the power level associated with proximal button (422), the operator may release proximal button (422). Alignment assembly (430) may then return proximal button (422) to the neutral position as described above with respect to FIG. 13.

To activate blade (152) via distal button (424), an operator may push distal button (424) toward the central longitudinal axis of shaft assembly (140). As can be seen in FIG. 15, the force is shown as being applied to an upper portion of distal button (424). However, it should be understood that an operator may apply a similar force at any point around the outer diameter of distal button (424) to achieve the same result of activating blade (152) at the power level associated with distal button (424).

As distal button (424) is pressed by an operator, distal button (424) moves laterally relative to body (412) of handle assembly (410) such that distal button (424) is displaced from the initial coaxial alignment to shaft assembly (140). The force applied by an operator is sufficient to overcome the resilient bias supplied by spring (439). Thus, as distal button (424) is displaced laterally, cam member (438) is driven proximally by the frustoconical shape of cam feature (428).

Continued displacement of distal button (424) eventually will result in physical contact between at least a portion of the inner diameter of distal button (424) and the outer diameter of outer sheath (142) of shaft assembly (140). Once contact is made between distal button (424) and outer sheath (142) of shaft assembly (140), electrical contact is made between the coating of distal button (424) and outer sheath (142). With such electrical contact, the activation circuit associated with distal button (424) is completed and thereby transitioned to a closed circuit state. With the activation circuit associated with distal button (424) in a closed circuit state, blade (152) is activated at a second predetermined power level. In some versions, this second power level is a relatively high power level.

It should be understood that activation of blade (152) may be accomplished as similarly described above with respect to circuit (210). For example, the activation circuit associated with distal button (424) may be a low voltage circuit in communication with a circuit board, similar to circuit board (216), which may in turn be in communication with to a generator that powers blade (152) via transducer (126) via waveguide (148).

Once an operator desires to switch power levels, or otherwise deactivate blade (152) at the power level associated with distal button (424), the operator may release distal button (424). Alignment assembly (430) may then return distal button (424) to the neutral position as described above with respect to FIG. 13.

C. Exemplary Alternative Handle Assembly with Internal Contact Switches

Figure 16:
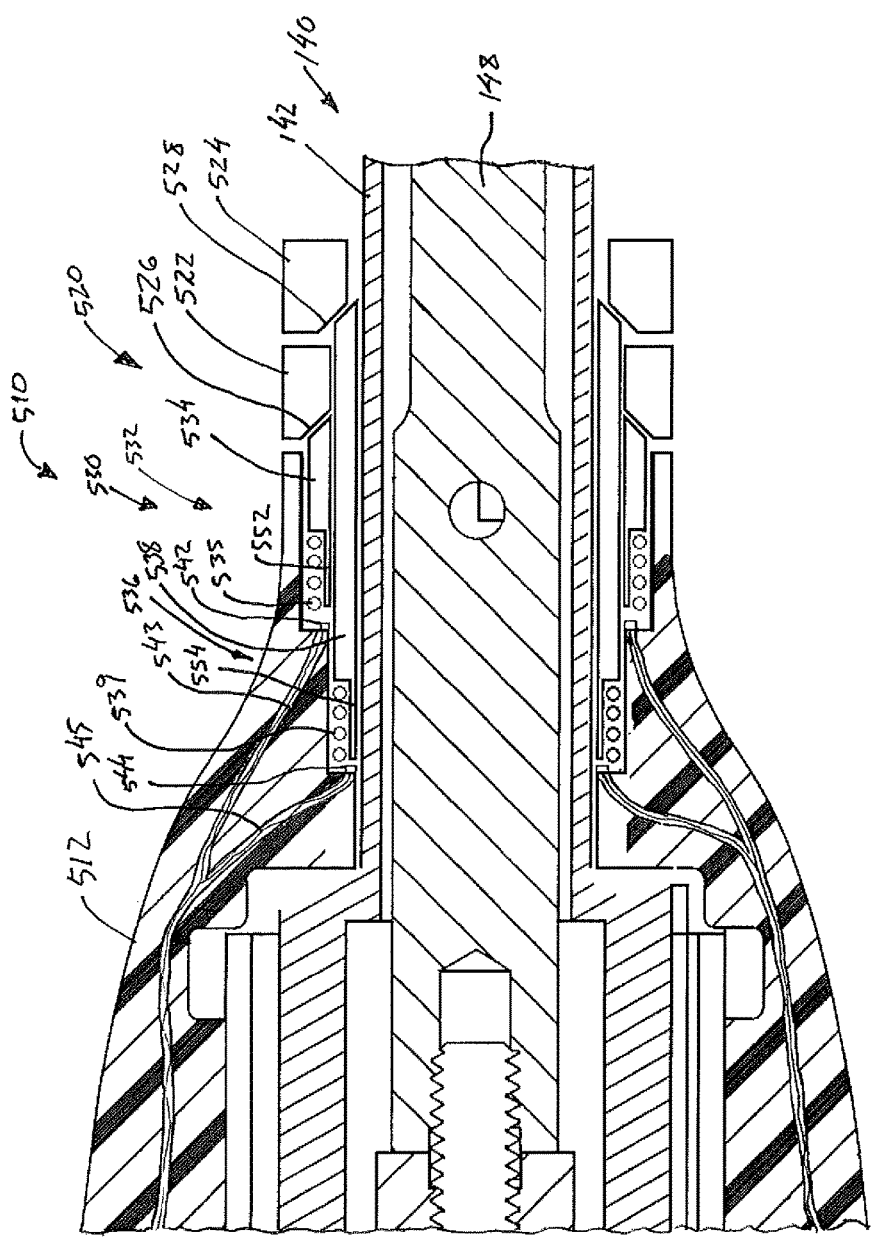
FIG. 16 depicts a side cross-sectional view of still another handle assembly that may be incorporated into the instrument of FIG. 2.

FIG. 16 shows still another exemplary alternative handle assembly (510) that may be readily incorporated into ultrasonic instrument (120) described above. Handle assembly (510) is substantially the same as handle assemblies (310, 410) described above, unless otherwise described herein. For instance, handle assembly (510) comprises a tubular elongate body (512). Like with handle assemblies (310, 410), handle assembly (510) supports shaft assembly (140), which includes an outer sheath projecting from the distal end of handle assembly (410).

Also like handle assemblies (310, 410), handle assembly (510) comprises a button assembly (520), which includes two discrete ring shaped buttons (522, 524) extending angularly around body (512) near the distal end of body (512). As will be described in greater detail below, each button (522, 524) is configured to be actuated radially inwardly from any angle around the perimeter of body (512) to activate blade (152) at one of two discrete power levels. Each button (522, 424) extends continuously about the perimeter of body (512). Moreover, each button (522, 524) has a discrete function in contrast to buttons (136), which have an identical function. In the present example, each button (522, 524) is rigid such that button (522, 524) will not deform (but will move as a rigid unit) in response to an operator pressing radially inwardly against button (522, 524). In some other versions, at least a portion of each button (522, 524) may be deformable.

Button assembly (520) is disposed coaxially about shaft assembly (140) at the distal end of body (512). Button assembly (520) comprises a proximal button (522), a distal button (524), and an alignment assembly (530). As described above, each button (522, 524) is generally ring shaped. The inside proximal diameter of each button (522, 524) includes a frustoconical cam feature (526, 528). As will be described in greater detail below, each cam feature (526, 528) is configured to engage with alignment assembly (530) to resiliently bias each button (522, 524) toward a position that is generally coaxial with shaft assembly (140).

Alignment assembly (530) comprises a separate alignment mechanism (532, 536) corresponding to each button (522, 524). Each alignment mechanism (532, 536) comprises a plurality of longitudinally translatable cam members (534, 538), which are resiliently biased distally by corresponding springs (535, 539). The distal end of each cam member (534, 538) is shaped to complement the frustoconical cam feature (526, 528) of the corresponding button (522, 524). Thus, as will be described in greater detail below, each cam member (534, 538) is configured to engage its corresponding button (522, 524) to resiliently bias the corresponding button (522, 524) toward a radial position of coaxial alignment with shaft assembly (140).

Unlike handle assemblies (310, 410) described above, handle assembly (510) does not utilize the internal diameter of buttons (522, 524) to activate blade (152). Instead, alignment assembly (530) is used to actuate contact switches (542, 544) mounted within body (512). In particular, handle assembly (510) comprises two contact switches (542, 544). Each contact switch (542, 544) corresponds to a particular button (522, 524). In the present example, contact switch (542) corresponds to proximal button (522), while contact switch (544) corresponds to distal button (524). Each contact switch (542, 544) is in communication with a respective set of wires (543, 545) that extend through body (512). Contact switches (542, 544) together with wires (543, 545) form two independent activation circuits that correspond to each button (522, 524).

Each contact switch (542, 545) is actuated using a corresponding cam member (534, 538). In particular, each cam member (534, 538) includes a proximally extending protrusion (552, 554). As will be described in greater detail below, each protrusion (542, 544) is configured to extend a distance proximally within body (512) to permit each protrusion (552, 554) to contact its corresponding contact switch (542, 544) when each respective cam member (534, 538) is driven proximally by each respective button (522, 524).

Figure 17:
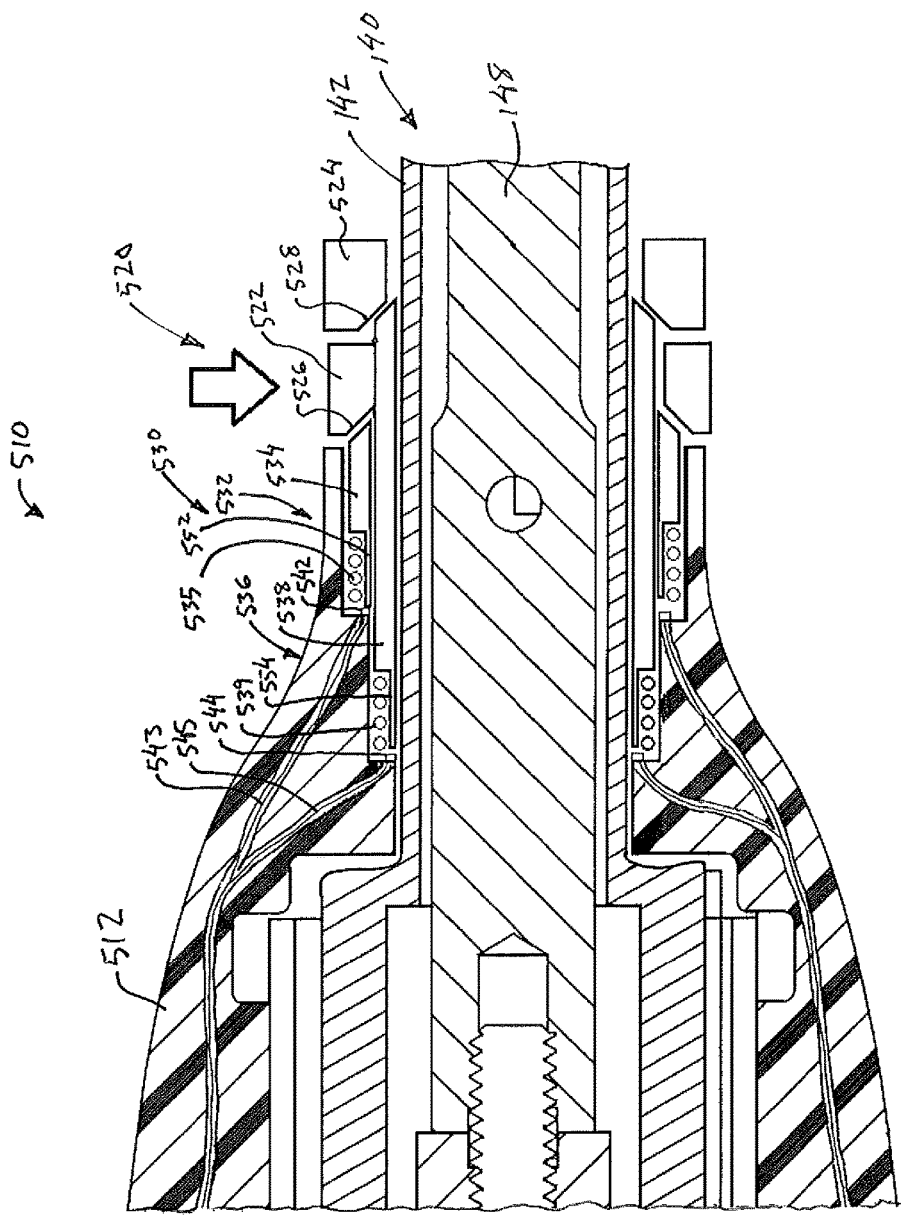
FIG. 17 depicts another side cross-sectional view of the handle assembly of FIG. 16, with a first activation ring in an activated position.
Figure 18:
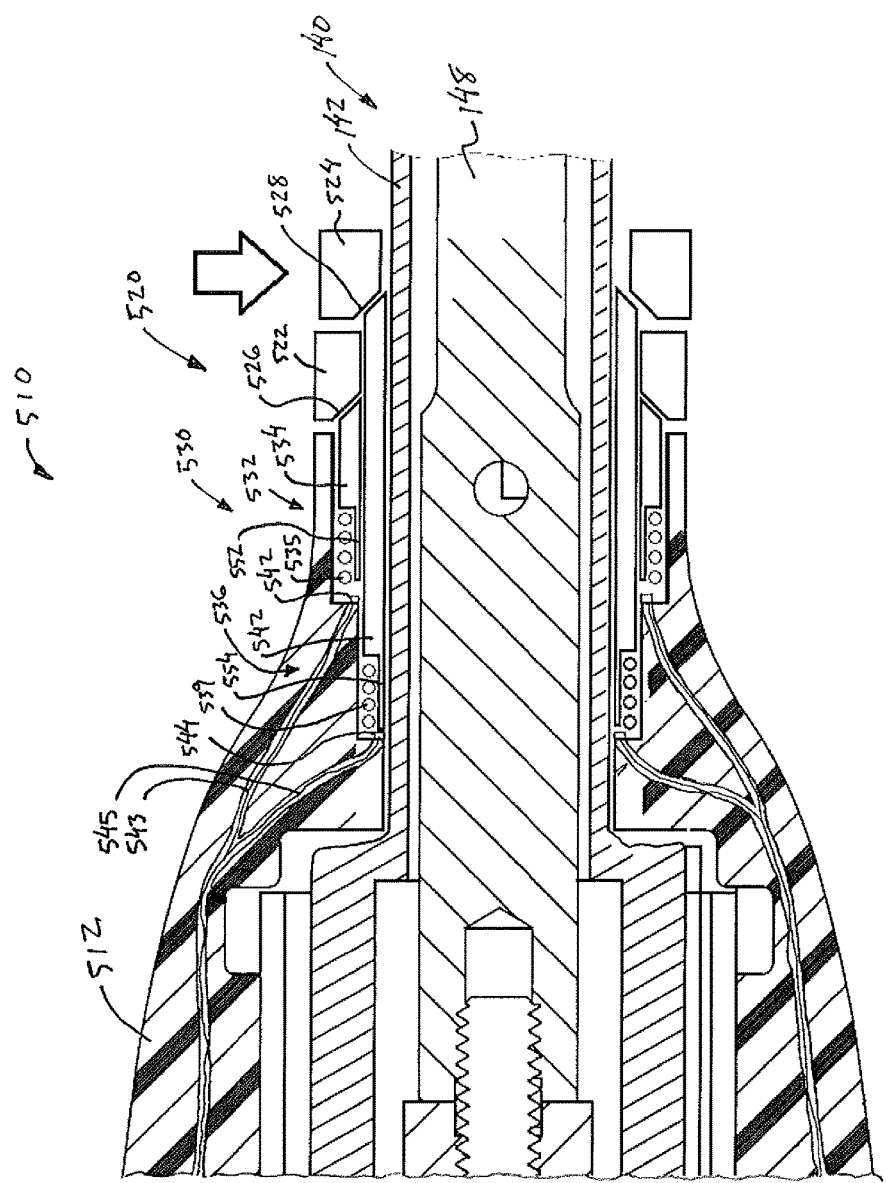
FIG. 18 depicts still another side cross-sectional view of the handle assembly of FIG. 15, with a second activation ring in an activated position.

FIGS. 16-18 depict an exemplary use of handle assembly (510) to activate blade (152) with ultrasonic energy and varying degrees of power. As can be seen in FIG. 16, buttons (522, 524) of button assembly (520) initially begin in a neutral position. In the neutral position, each alignment mechanism (532, 536) of alignment assembly (530) generally acts on each corresponding button (522, 524) to align each button (522, 524) coaxially with shaft assembly (140). In particular, each cam member (534, 538) is resiliently biased distally by each cam member's (534, 538) respective spring (535, 539). The distal end of each cam member (534, 538) in turn acts on cam feature (526, 528) of each respective button (522, 524). This engagement between cam members (534, 538) and cam features (526, 528) generates an outwardly oriented force on buttons (522, 524). This outwardly oriented force is uniform about the entire circumference of each cam member (534, 538). Thus, because cam members (534, 538) extend along a full circle within the inner diameter associated with button (522, 524), the net force resiliently biases each button (522, 524) laterally toward a position that is coaxial with the central longitudinal axis of shaft assembly (140).

When proximal button (522) is in the neutral position, cam member (534) is disposed distally and there is no contact between protrusion (552) and contact switch (542). Likewise, when distal button (524) is in the neutral position, cam member (538) is disposed distally and there is no contact between protrusion (554) and contact switch (544).

Thus the activation circuits associated with buttons (422, 424) are in an open circuit state. When each activation circuit is in the open circuit state, blade (152) is inactive and not ultrasonically energized.

To activate blade (152) via proximal button (522), an operator may push proximal button (522) toward the central longitudinal axis of shaft assembly (140). As can be seen in FIG. 17, the force is shown as being applied to an upper portion of proximal button (522). However, it should be understood that an operator may apply a similar force at any point around the outer diameter of proximal button (522) to achieve the same result of activating blade (152) at the power level associated with proximal button (522).

As proximal button (522) is pressed by an operator, proximal button (522) moves laterally relative to body (512) of handle assembly (510) such that proximal button (522) is displaced from the initial coaxial alignment with shaft assembly (140). The force applied by an operator is sufficient to overcome the resilient bias supplied by spring (535). Thus, as proximal button (522) is displaced laterally, cam member (434) is driven proximally by the frustoconical shape of cam feature (526).

Continued displacement of proximal button (522) will eventually result in physical contact between protrusion (552) of cam member (534) and contact switch (542). Once contact is made between protrusion (552) of cam member (534) and contact switch (542), the activation circuit associated with proximal button (522) is completed and thereby transitioned to a closed circuit state. With the activation circuit associated with proximal button (522) in a closed circuit state, blade (152) is activated at a first predetermined power level. In some versions, this first power level is a relatively low power level.

It should be understood that activation of blade (152) may be accomplished as similarly described above with respect to circuit (210). For example, the activation circuit associated with proximal button (522) may be a low voltage circuit in communication with a circuit board, similar to circuit board (216), which may in turn be in communication with to a generator that powers blade (152) via transducer (126) via waveguide (148).

Once an operator desires to deactivate blade (152) from the power level associated with proximal button (522), the operator may release proximal button (522). Alignment assembly (530) may then return proximal button (522) to the neutral position as described above with respect to FIG. 16.

To activate blade (152) via distal button (524), an operator may push distal button (524) toward the central longitudinal axis of shaft assembly (140). As can be seen in FIG. 18, the force is shown as being applied to an upper portion of distal button (524). However, it should be understood that an operator may apply a similar force at any point around the outer diameter of distal button (524) to achieve the same result of activating blade (152) at the power level associated with distal button (524).

As distal button (524) is pressed by an operator, distal button (524) moves laterally relative to body (512) of handle assembly (510) such that distal button (524) is displaced from the initial coaxial alignment with shaft assembly (140). The force applied by an operator is sufficient to overcome the resilient bias supplied by spring (539). Thus, as distal button (524) is displaced laterally, cam member (538) is driven proximally by the frustoconical shape of cam feature (528).

Continued displacement of distal button (524) eventually will result in physical contact between protrusion (554) of cam member (538) and contact switch (544). Once contact is made between protrusion (554) of cam member (538) and contact switch (544), the activation circuit associated with distal button (524) is completed and thereby transitioned to a closed circuit state. With the circuit associated with distal button (524) in a closed circuit state, blade (152) is activated at a second predetermined power level. In some versions, this second power level is a relatively high power level.

It should be understood that activation of blade (152) may be accomplished as similarly described above with respect to circuit (210). For example, the activation circuit associated with distal button (524) may be a low voltage circuit in communication with a circuit board, similar to circuit board (216), which may in turn be in communication with to a generator that powers blade (152) via transducer (126) via waveguide (148).

Once an operator desires to switch power levels, or otherwise deactivate blade (152) at the power level associated with distal button (524), the operator may release distal button (524). Alignment assembly (530) may then return distal button (524) to the neutral position as described above with respect to FIG. 16.

IV. Exemplary Button Lock Features

In some instances it may be desirable to lock out actuation of activation features of a handle assembly similar to handle assemblies (310, 410, 510) described above. For instance, with a set of buttons similar to buttons (322, 324, 422, 424, 522, 524) described above so accessible to an operator, inadvertent activation may be possible. Accordingly, it may be desirable to incorporate features into a handle assembly to prevent inadvertent activation or otherwise lock out the instrument. While various additional handle assembly features are described below, it should be understood that other examples will be apparent to those of ordinary skill in the art in view of the teachings herein. It should be further understood that to the extent that the various features and/or structures are described with respect to a particular handle assembly, the same features and/or structures may be readily incorporated into other handle assemblies described herein.

A. Exemplary Removable Insert Lock Feature

Figure 19:
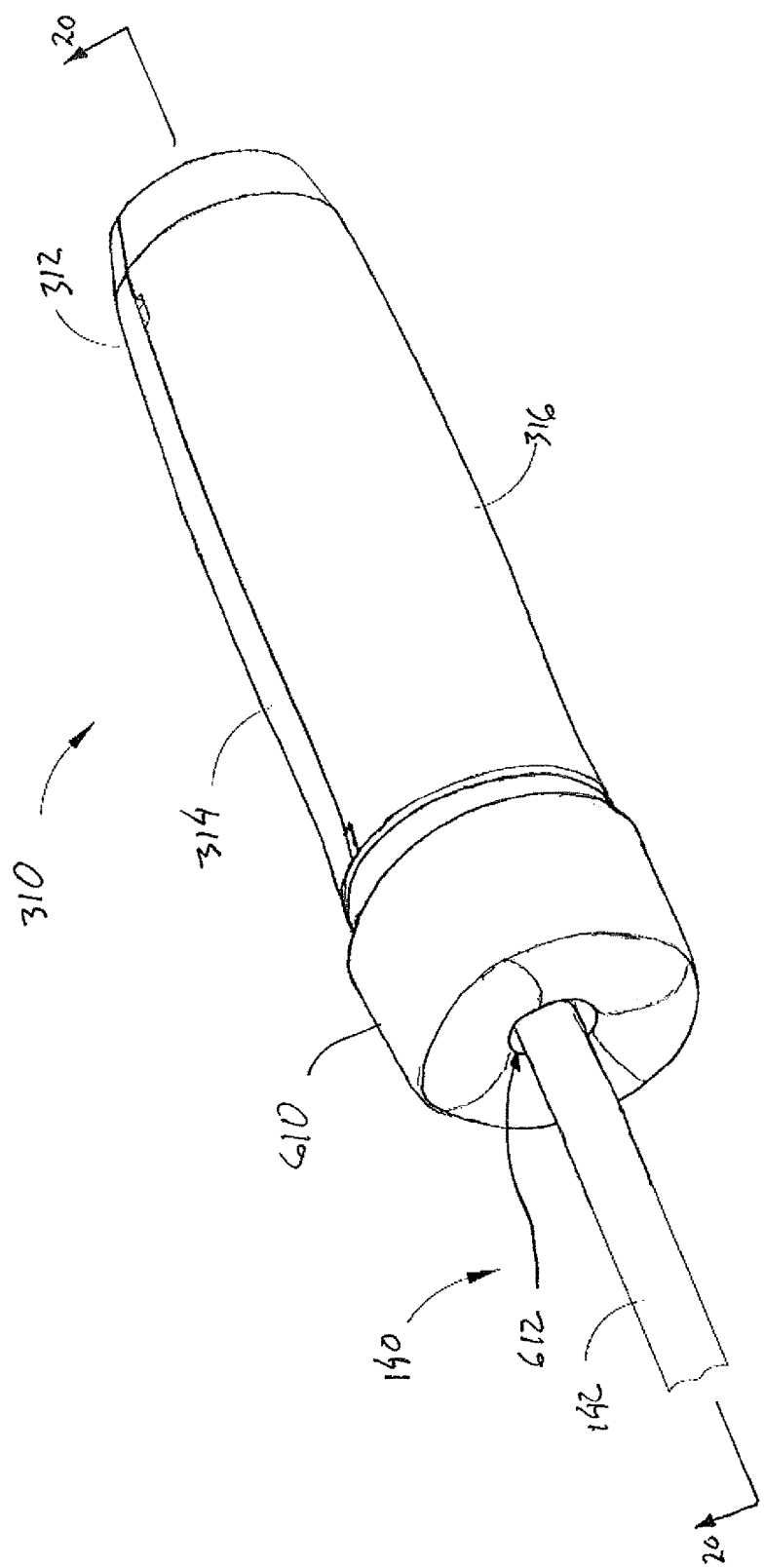
FIG. 19 depicts a front perspective view of the handle assembly of FIG. 4, with the handle assembly equipped with a lock insert.

FIG. 19 shows handle assembly (310), described above, equipped with an exemplary lock sleeve (610). Lock sleeve (610) is generally configured to prevent actuation of buttons (322, 324) of handle assembly (310), as will be described in greater detail below. Lock sleeve (610) comprises a single polycarbonate or other electrically insulating material. Lock sleeve (610) is shaped for insertion into a gap between shaft assembly (140) and buttons (322, 324). To accommodate the distal extension of shaft assembly (140), lock sleeve (610) is generally donut shaped with a central opening (612) disposed on the distal end of lock sleeve (610). The proximal end of lock sleeve is generally open to permit positioning of lock sleeve (610) over buttons (322, 324).

Figure 20:
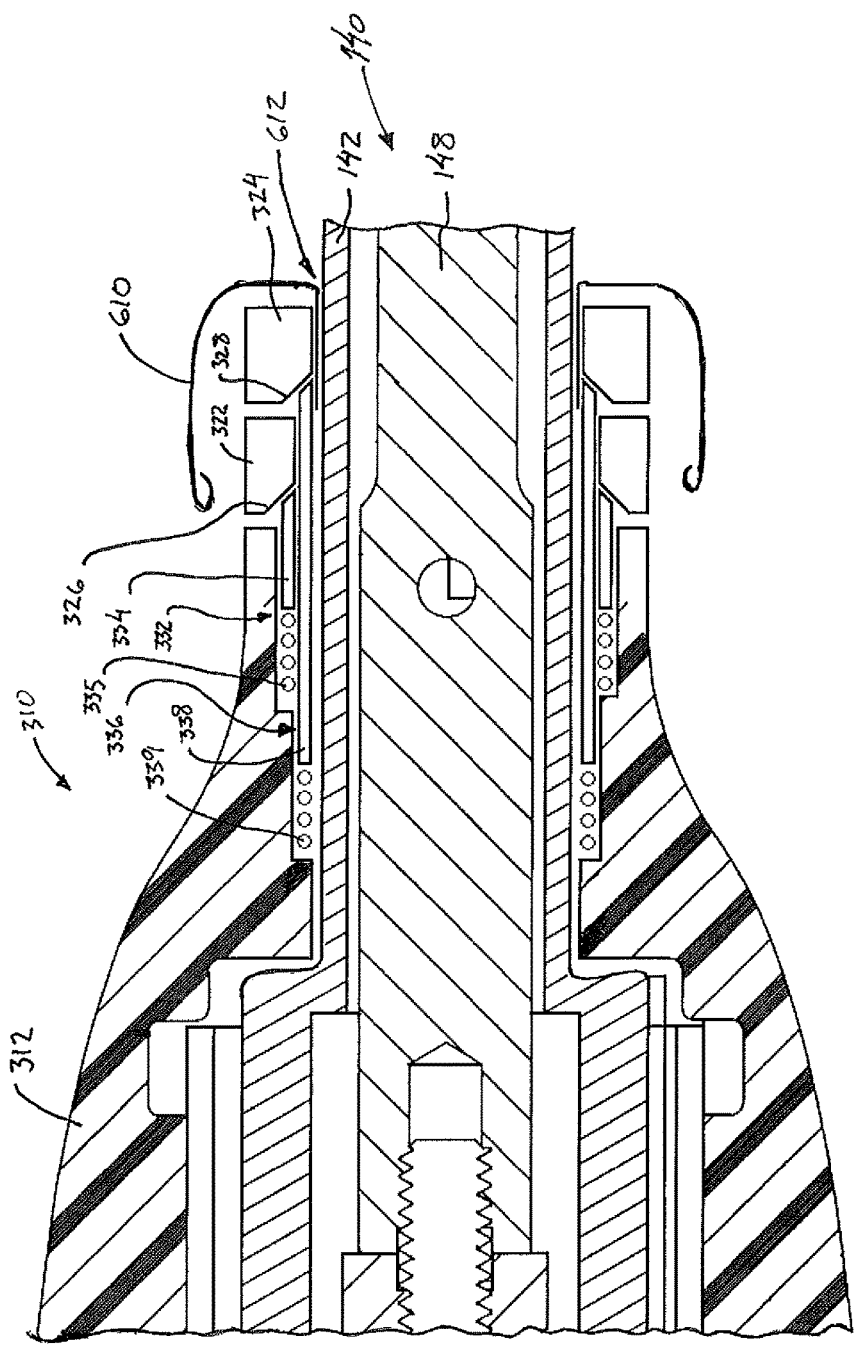
FIG. 20 depicts a side cross-sectional view of the handle assembly of FIG. 19, with the cross-section taken along line 20-20 of FIG. 19.

As can be seen in FIG. 20, lock sleeve (610) is shaped to cover buttons (322, 324) and curves around the distal end of handle assembly (310) and into the gap between shaft assembly (140) and buttons (322, 324). Accordingly, lock sleeve (610) covers outer sheath (142) of shaft assembly (140), thereby preventing contact between outer sheath (142) and buttons (322, 324). As described above, buttons (322, 324) include electrical contacts (344) on their inner diameter that create a closed activation circuit condition when contact occurs between buttons (322, 324) and outer sheath (142). Thus, lock sleeve (610) prevents creation of a closed activation circuit condition by preventing contact between buttons (322, 324) and outer sheath (142). Additionally, in some examples lock sleeve (610) has a thickness suitable to prevent substantially all lateral movements of buttons (322, 324). Therefore, in some examples lock sleeve (610) also acts as a physical stop to prevent lateral movement of buttons (322, 324).

Figure 21:
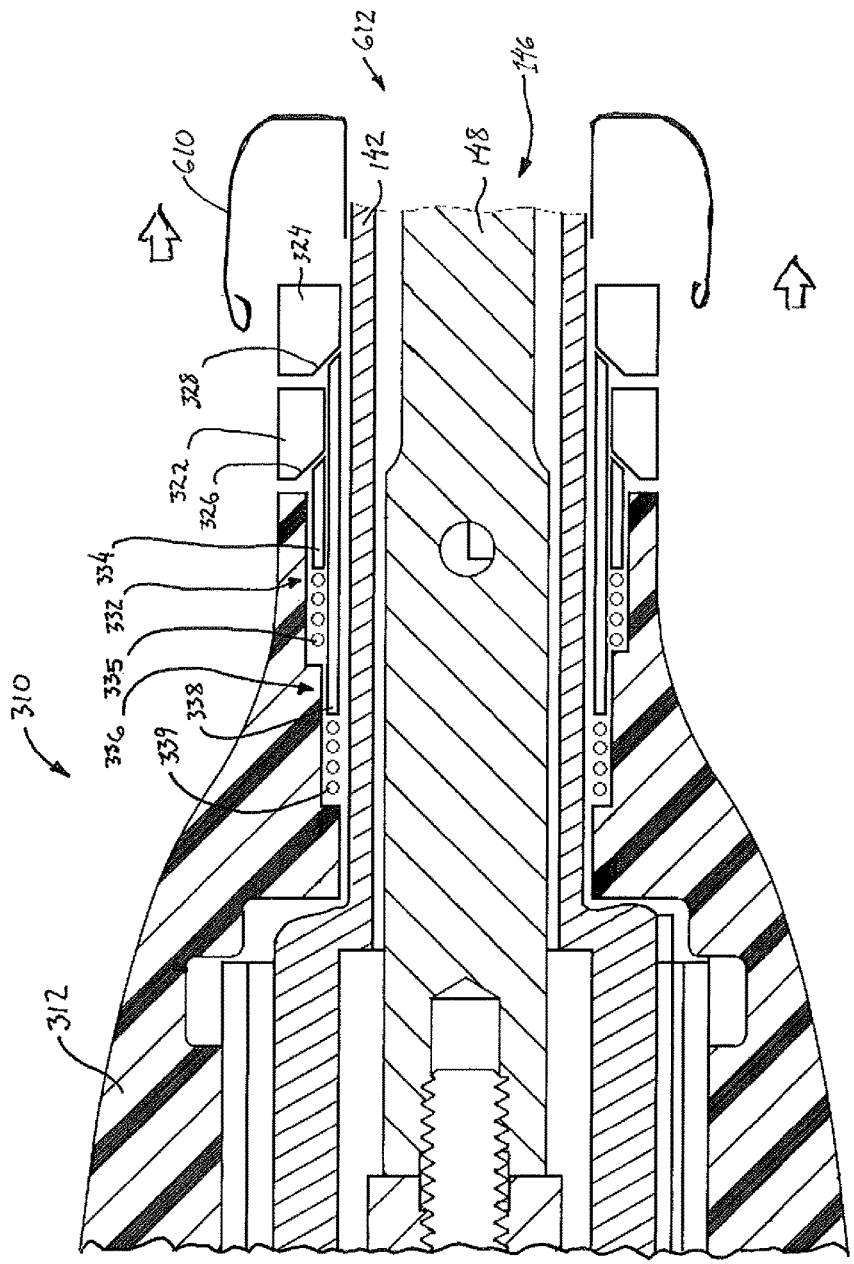
FIG. 21 depicts another side cross-sectional view of the handle assembly of FIG. 19, with a lock insert removed.

To disengage lock sleeve (610), an operator may simply pull lock sleeve (610) distally along shaft assembly (140) as shown in FIG. 21. With lock sleeve (610) removed, buttons (322, 324) regain the functionality described above with respect to FIGS. 4-9. In some versions, lock sleeve (610) is pulled distally all the way off of shaft assembly (140) such that lock sleeve (610) is fully separated from the rest of the instrument. In some other versions, lock sleeve (610) is simply pulled distally enough to enable free actuation of buttons (322, 324) and is then released, such that lock sleeve (610) remains disposed at a distal position on shaft assembly (140).

It should also be understood that various features may be used to selectively retain the position of lock sleeve (610) in the locking position shown in FIG. 20. For instance, lock sleeve (610) may resiliently bear against outer sheath (142) to provide friction that holds lock sleeve (610) in place in the proximal position. Alternatively, an o-ring, elastomeric washer, or similar feature may be positioned about outer sheath (142), either inside lock sleeve (610) or distal to (but adjacent to) lock sleeve (610); and such a feature may provide sufficient resistance to prevent inadvertent distal movement of lock sleeve (610) while permitting intentional distal movement of lock sleeve (610). Other suitable features and methods for selectively retaining positioning of lock sleeve (610) will be apparent to those of ordinary skill in the art in view of the teachings herein.

Although lock sleeve (610) is shown as having a particular shape, it should be understood that lock sleeve (610) may take on numerous other shapes. For instance, in some examples lock sleeve (610) does not cover buttons (322, 324). Instead, lock sleeve (610) extends outwardly away from shaft assembly (140). Of course, numerous suitable alternative shapes for lock sleeve (610) will be apparent to those of ordinary skill in the art in view of the teachings herein.

B. Exemplary Spring Biased Lock Feature

Figure 22:
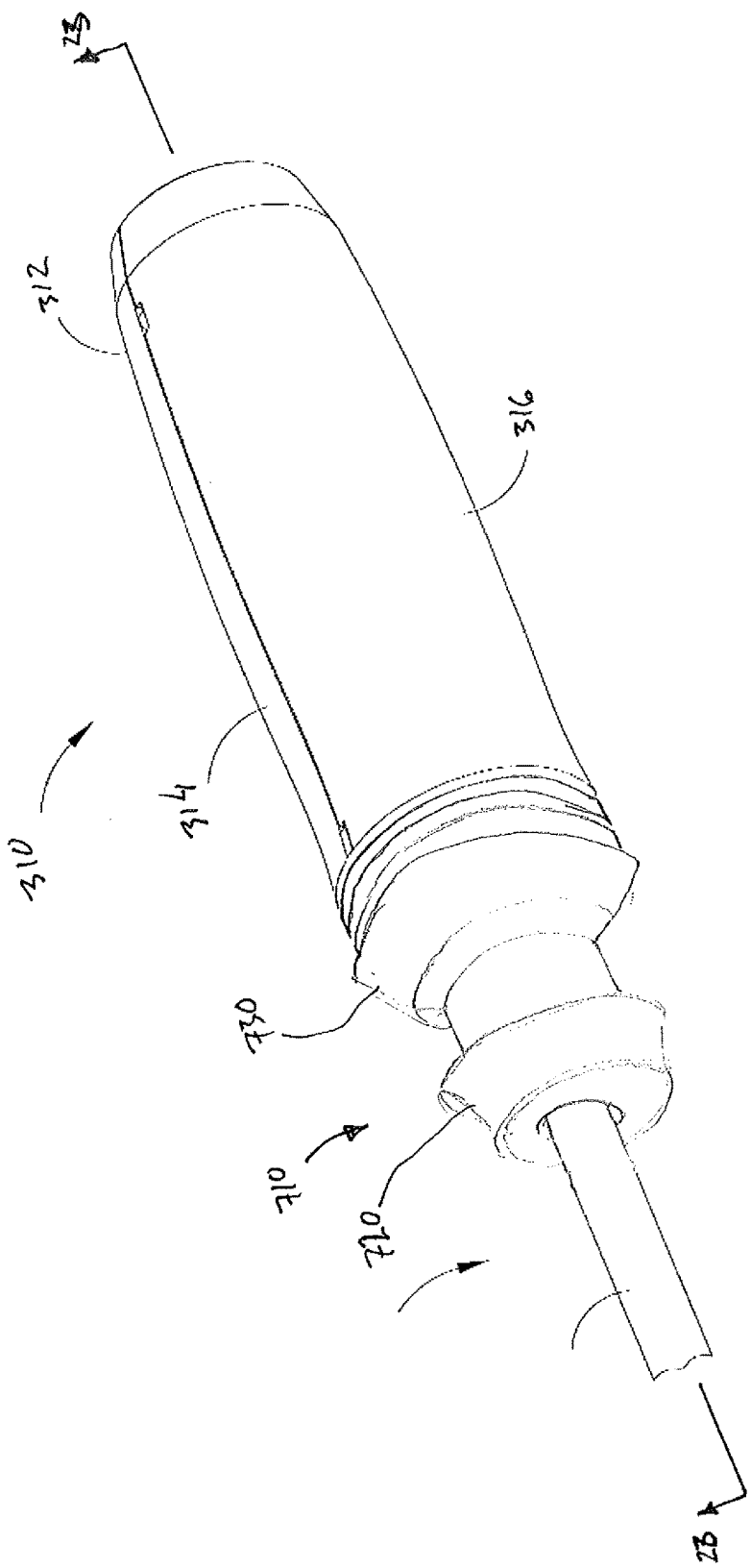
FIG. 22 depicts a perspective view of yet another exemplary alternative handle assembly that may be incorporated into the instrument of FIG. 2.
Figure 23:
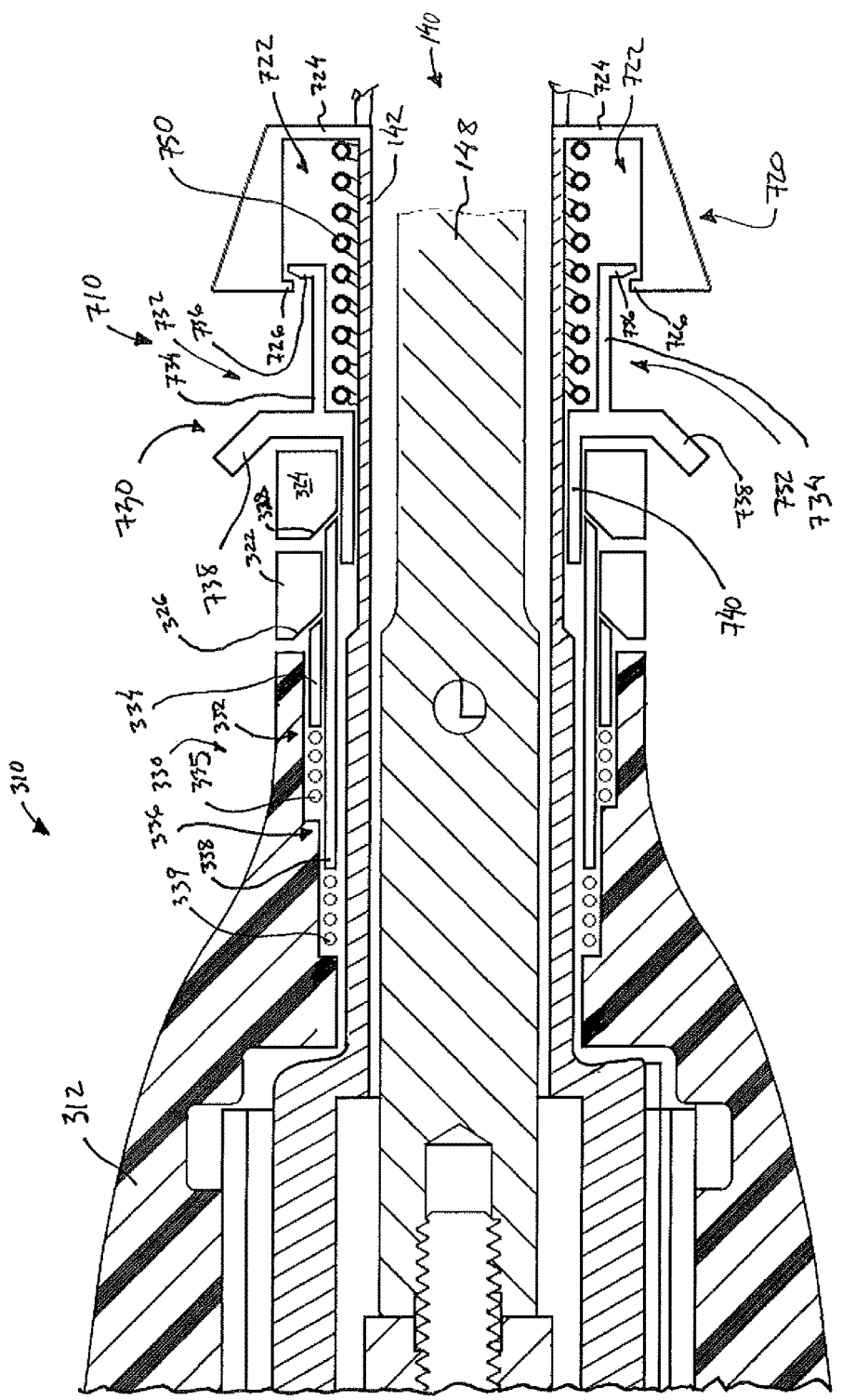
FIG. 23 depicts a side cross-sectional view of the handle assembly of FIG. 22, with the cross-section taken along line 23-23 of FIG. 22.

FIG. 22 shows handle assembly (310), described above, equipped with an exemplary lock assembly (710). Unlike lock sleeve (610) described above, lock assembly (710) is not removable. Instead, lock assembly (710) is generally movable by an operator to selectively lock and unlock buttons (322, 324). Lock assembly (710) comprises a grounding member (720), a lock member (730), and a spring (750) disposed between grounding member (720) and lock member (730). As best seen in FIG. 23, grounding member (720) is integral with outer sheath (142) of shaft assembly (140). Alternatively, in some examples grounding member (720) may be a separate component that is independent from outer sheath (142).

Grounding member (720) generally forms a longitudinally fixed platform, which restricts the motion of lock member (730) relative to body (312) of handle assembly (310). In particular, grounding member (720) defines a translation cavity (722) that permits translation of lock member (730) within the confines of grounding member (720). Grounding member (720) further includes a distal stop portion (724) and a proximal annular flange (726). Distal stop portion (724) and proximal annular flange (726) together define a translation distance for lock member (730). As will be described in greater detail below, lock member (730) is generally free to translate within the longitudinal space defined between distal stop portion (724) and proximal annular flange (726).

Lock member (730) includes a translation member (732), a drive portion (738), and a button lock portion (740). Translation member (732) is generally configured to engage with grounding member (720). As will be described in greater detail below, translation member (732) is slidable through a predetermined range of motion within translation cavity (722) of lock member (730) to define the translation limits of lock member (730). Translation member (732) includes a longitudinal portion (734) and an outwardly extending annular flange (736).

Longitudinal portion (734) extends distally from drive portion (738) for a length approximately corresponding to the length of button lock portion (740). As will be understood, the length of longitudinal portion (734) permits button lock portion (740) to translate into and out of a gap between buttons (322, 324) and shaft assembly (142). Longitudinal portion (734) is configured with a diameter that is larger relative to button lock portion (740). Such a diameter permits spring (750) to be accommodated within the inner diameter of longitudinal portion (734).

Flange (736) extends outwardly from longitudinal portion (734). Flange (736) is sized to fit within cavity (722) defined by grounding member (720). Flange (736) is additionally sized to engage with corresponding flange (726) of grounding member (720). This sizing maintains translation member (732) within cavity (722) of grounding member (720) and guides translation member (732) along a predefined translation path.

Drive portion (738) is configured for grasping and/or manipulation by an operator. Drive portion (738) is disposed between longitudinal portion (734) and button lock portion (740). In the present example, drive portion (738) includes a slight proximal orientation to cover at least some of buttons (322, 324) when in a locked state. Although this feature is merely optional, in some instances it may be desirable to provide a visual indicator to an operator that lock assembly (710) is in a locked state.

Button lock portion (740) extends proximally from drive portion (738). Button lock portion (740) is configured to slide between the gap between buttons (322, 324) and shaft assembly (140). As will be described in greater detail below, when button lock portion (740) is disposed between buttons (322, 324) and shaft assembly (140) lateral movement of buttons (322, 324) is physically arrested. Moreover, in some examples button lock portion (740) may comprise an electrically insulating material to prevent electrical conductivity between buttons (322, 324) and shaft assembly (140).

FIGS. 23 and 24 show an exemplary use of lock assembly (710). As can be seen in FIG. 23, lock assembly (710) is initially positioned in a locked state. In the locked state, lock member (730) is resiliently biased proximally by spring (750) such that button lock portion (740) is disposed between buttons (322, 324) and shaft assembly (140). This positioning locks buttons (322, 324) by two simultaneous mechanisms. First, button lock portion (740) electrically insulates outer sheath (142) of shaft assembly (140). As described above, buttons (322, 324) operate by closing an activation circuit when brought into contact with outer sheath (142) of shaft assembly (140). Thus, button lock portion (740) prevents closure of any activation circuits associated with buttons (322, 324) by electrically insulating outer sheath (142) relative to buttons (322, 324). Second, button lock portion (740) provides a mechanical stop for buttons (322, 324) by filling the gap between buttons (322, 324) and shaft assembly (140).

To unlock the functionality of buttons (322, 324) described above, an operator may exert a force on drive portion (738) to push lock member (730) distally, thereby overcoming the resilient bias of spring (750). Such a force will transition lock member (730) from the position shown in FIG. 23 to the position shown in FIG. 24. Once lock member (730) is in the position shown in FIG. 24, lock assembly (710) is in an unlocked state.

When lock assembly (710) is transitioning to the unlocked state, lock member (730) is generally permitted to translate through a predetermined distance defined by grounding member (720). In particular, longitudinal portion (734) of translation member (732) translates within cavity (722) of grounding member (720) until flange (736) contacts distal stop portion (724) of grounding member (720). Further translation of lock member (730) is prevented by contact between flange (736) and distal stop portion (724).

Once lock assembly (710) is transitioned to the unlocked state, buttons (322, 324) may be actuated as described above with respect to FIGS. 4-9. After an operator is finished actuating buttons (322, 324) as desired, the operator may release any force from drive portion (738). With such force released, lock member (730) will automatically transition back to the locked position of FIG. 22 by the resilient bias of spring acting on drive portion (738).

It should be understood that, in the present example, the operator must maintain a distally oriented force on lock member (730) (overcoming the proximal bias of spring (750)) to enable actuation of buttons (322, 325). In some other versions, lock assembly (710) comprises detent features, latching features, and/or other features that selectively retain lock member (730) in a distal position (FIG. 24). In such versions, the operator may simply advance lock member (730) to this distal position and then release lock member (730) without having to continue pressing distally on lock member to enable actuation of buttons (322, 325). If desired, when the operator is finished actuation buttons (322, 325), the operator may release lock member (730) from the holding feature(s), which will allow spring (750) to drive lock member (730) back to the proximal position (FIG. 23). Various suitable features that may be used to selectively retain a longitudinal position of lock member (730) will be apparent to those of ordinary skill in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body, wherein the body defines a longitudinal axis, wherein the body is configured to receive an ultrasonic transducer; (b) an actuation assembly, wherein the actuation assembly comprises: (i) at least one annular activation member, wherein the at least one annular activation member extends angularly about the body along a 360 degree angular range, wherein the at least one annular activation member is configured to move laterally relative to the longitudinal axis of the body, and (ii) at least one activation circuit corresponding to the at least one annular activation member; (c) a shaft assembly, wherein the shaft assembly comprises an acoustic waveguide; and (d) an ultrasonic blade, wherein the ultrasonic blade is in acoustic communication with the acoustic waveguide, wherein the at least one activation circuit is configured to activate the ultrasonic blade in response to lateral movement of the activation member relative to the longitudinal axis of the body.

Example 2

The ultrasonic instrument of Example 1, wherein the at least one annular activation member comprises a first annular activation member and a second annular activation member, wherein the at least one activation circuit comprises a first activation circuit and a second activation circuit, wherein the first annular activation member corresponds to the first activation circuit and the second annular activation member corresponds to the second activation circuit.

Example 3

The ultrasonic instrument of Example 2, wherein the first activation circuit is configured to transition from an open state to a closed state in response to lateral movement of the first annular activation member, wherein the second activation circuit is configured to transition from an open state to a closed state in response to lateral movement of the second annular activation member.

Example 4

The ultrasonic instrument of any one or more of Examples 2 through 3, wherein the first activation circuit is configured to activate the ultrasonic blade at a first energy level in response to lateral movement of the first activation member, wherein the second activation circuit is configured to activate the ultrasonic blade at a second energy level in response to lateral movement of the second activation member.

Example 5

The ultrasonic instrument of any one or more of Examples 1 through 5, wherein the at least one annular activation member comprises a circular ring extending about the body.

Example 6

The ultrasonic instrument of Example 5, wherein the circular ring comprises a conical portion.

Example 7

The ultrasonic instrument of Example 6, further comprising at least one actuation member, wherein the at least one actuation member is configured to bear against the conical portion of the circular ring to resiliently bias the at least one annular activation member toward a position that is coaxially aligned with the body.

Example 8

The ultrasonic instrument of any one or more of Examples 1 through 7, wherein the at least one activation circuit comprises a first conductor and a second conductor, wherein the at least one annular activation member is configured to place the first conductor into contact with the second conductor.

Example 9

The ultrasonic instrument of Example 8, wherein the at least one activation circuit is configured to transition from the open circuit condition to the closed circuit condition in response to contact between the first conductor and the second conductor.

Example 10

The ultrasonic instrument of any one or more of Examples 1 through 9, further comprising a lock feature, wherein the lock feature is configured to prevent the at least one activation circuit from activating the ultrasonic blade.

Example 11

The ultrasonic instrument of Example 10, wherein the lock feature is configured to selectively electrically insulate the at least one annular activation member relative to the shaft assembly.

Example 12

The ultrasonic instrument of any one or more of Examples 10 through 11, wherein the lock feature is configured to selectively impede lateral movement of the at least one annular activation member relative to the longitudinal axis of the body.

Example 13

The ultrasonic instrument of any one or more of Examples 1 through 12, wherein the actuation assembly further comprises a cam feature, wherein the cam feature is configured to translate proximally in response to lateral movement of the at least one annular activation member relative to the longitudinal axis of the body.

Example 14

The ultrasonic instrument of Example 13, wherein the actuation assembly further comprises a contact switch, wherein the contact switch is in communication with the at least one activation circuit, wherein the at least one annular activation member is configured to actuate the contact switch directly or via the cam feature.

Example 15

The ultrasonic instrument of Example 14, wherein the cam feature is configured to engage the contact switch in response to lateral movement of the at least one annular activation member relative to the longitudinal axis of the body, wherein the contact switch is configured to transition the at least one activation circuit to a closed circuit condition when engaged with the cam feature.

Example 16

The ultrasonic instrument of Example 15, wherein the cam feature is resiliently biased to urge the at least one annular activation member into coaxial alignment with the longitudinal axis of the body, wherein the at least one annular activation member is operable to drive the cam feature proximally into engagement with the contact switch in response to lateral movement of the at least one annular activation member relative to the longitudinal axis of the body.

Example 17

An ultrasonic instrument comprising: (a) a body, wherein the body defines a longitudinal axis, wherein the body is configured to receive an ultrasonic transducer; (b) an actuation assembly, wherein the actuation assembly comprises: (i) at least one activation ring disposed coaxially with the longitudinal axis of the body, and (ii) at least one activation circuit, wherein the at least one activation circuit is associated with the at least one activation ring, wherein the at least one activation circuit is responsive to transverse movement of the at least one activation ring relative to the longitudinal axis of the body to transition between an open circuit condition and a closed circuit condition; (c) a shaft assembly, wherein the shaft assembly comprises an acoustic waveguide; and (d) an ultrasonic blade, wherein the ultrasonic blade is in acoustic communication with the acoustic waveguide, wherein the at least one activation circuit is operable to trigger activation of the acoustic waveguide.

Example 18

The ultrasonic instrument of Example 17, wherein the actuation assembly further comprises a centering assembly, wherein the centering assembly is configured to resiliently bias the activation ring toward a position of coaxial alignment with the longitudinal axis of the body.

Example 19

The ultrasonic instrument of any one or more of Examples 17 through 18, wherein the at least one activation ring includes a conductor, wherein the at least one circuit is in electrical communication with the conductor and at least a portion of the shaft assembly, wherein the at least one activation circuit is configured to transition to the closed circuit condition in response to movement of the activation ring into contact with at least a portion of the shaft assembly.

Example 20

An ultrasonic instrument comprising: (a) a body, wherein the body defines a longitudinal axis, wherein the body is configured to receive an ultrasonic transducer; (b) an actuation assembly, wherein the actuation assembly comprises: (i) a annular activation member assembly, wherein the annular activation member assembly comprises a first annular activation member and a second annular activation member, wherein the first and second annular activation members are disposed around the longitudinal axis of the body, and (ii) an activation circuit assembly, wherein the activation circuit assembly includes a first activation circuit and a second activation circuit, wherein the first activation circuit is associated with the first annular activation member, wherein the second activation circuit is associated with the second annular activation member, wherein the activation circuit assembly is configured to transition to an active state in response to lateral translation of the first annular activation member or the second annular activation member relative to the longitudinal axis of the body; (c) a shaft assembly, wherein the shaft assembly comprises an acoustic waveguide; and (d) an ultrasonic blade, wherein the ultrasonic blade is in acoustic communication with the acoustic waveguide, wherein the activation circuit assembly is operable to trigger activation of the acoustic waveguide.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An ultrasonic instrument comprising:
   (a) a body, wherein the body defines a longitudinal axis, wherein the body is configured to receive an ultrasonic transducer,
   (b) an actuation assembly, wherein the actuation assembly comprises:
      (i) at least one annular activation member, wherein the at least one annular activation member extends angularly about the body along a 360 degree angular range, wherein the at least one annular activation member is configured to move laterally relative to the longitudinal axis of the body, and
      (ii) at least one activation circuit corresponding to the at least one annular activation member;
   (c) a shaft assembly, wherein the shaft assembly comprises an acoustic waveguide;
   (d) an ultrasonic blade, wherein the ultrasonic blade is in acoustic communication with the acoustic waveguide, wherein the at least one activation circuit is configured to activate the ultrasonic blade in response to lateral movement of the at least one annular activation member relative to the longitudinal axis of the body; and (e) a camming assembly encompassing at least a portion of the ultrasonic waveguide, wherein the camming assembly is configured to resiliently bias the at least one annular activation member toward a position that is coaxially aligned with the body.

2. The ultrasonic instrument of claim 1, wherein the at least one annular activation member comprises a first annular activation member and a second annular activation member, wherein the at least one activation circuit comprises a first activation circuit and a second activation circuit, wherein the first annular activation member corresponds to the first activation circuit and the second annular activation member corresponds to the second activation circuit.

3. The ultrasonic instrument of claim 2, wherein the first activation circuit is configured to transition from an open state to a closed state in response to lateral movement of the first annular activation member, wherein the second activation circuit is configured to transition from an open state to a closed state in response to lateral movement of the second annular activation member.

4. The ultrasonic instrument of claim 2, wherein the first activation circuit is configured to activate the ultrasonic blade at a first energy level in response to lateral movement of the first activation member, wherein the second activation circuit is configured to activate the ultrasonic blade at a second energy level in response to lateral movement of the second activation member.

5. The ultrasonic instrument of claim 1, wherein the at least one annular activation member comprises a circular ring extending about the body.

6. The ultrasonic instrument of claim 5, wherein the circular ring comprises a conical portion.

7. The ultrasonic instrument of claim 6, wherein the caroming assembly comprises at least one actuation member, wherein the at least one actuation member is configured to bear against the conical portion of the circular ring to resiliently bias the at least one annular activation member toward the position that is coaxially aligned with the body.

8. The ultrasonic instrument of claim 1, wherein the at least one activation circuit comprises a first conductor and a second conductor, wherein the at least one annular activation member is configured to place the first conductor into contact with the second conductor.

9. The ultrasonic instrument of claim 8, wherein the at least one activation circuit is configured to transition from the open circuit condition to the closed circuit condition in response to contact between the first conductor and the second conductor.

10. The ultrasonic instrument of claim 1, further comprising a lock feature, wherein the lock feature is configured to prevent the at least one activation circuit from activating the ultrasonic blade.

11. The ultrasonic instrument of claim 10, wherein the lock feature is configured to selectively electrically insulate the at least one annular activation member relative to the shaft assembly.

12. The ultrasonic instrument of claim 10, wherein the lock feature is configured to selectively impede lateral movement of the at least one annular activation member relative to the longitudinal axis of the body.

13. The ultrasonic instrument of claim 1, wherein the camming assembly is configured to translate proximally in response to lateral movement of the at least one annular activation member relative to the longitudinal axis of the body.

14. The ultrasonic instrument of claim 13, wherein the actuation assembly further comprises a contact switch, wherein the contact switch in communication with the at least one activation circuit, wherein the at least one annular activation member is configured to actuate the contact switch directly or via the camming assembly.

15. The ultrasonic instrument of claim 14, wherein the camming assembly is configured to engage the contact switch in response to lateral movement of the at least one annular activation member relative to the longitudinal axis of the body, wherein the contact switch is configured to transition the at least one activation circuit to a closed circuit condition when engaged with the camming assembly.

16. The ultrasonic instrument of claim 15, wherein the camming assembly is resiliently biased to urge the at least one annular activation member into coaxial alignment with the longitudinal axis of the body, wherein the at least one annular activation member is operable to drive the camming assembly proximally into engagement with the contact switch in response to lateral movement of the at least one annular activation member relative to the longitudinal axis of the body.

17. An ultrasonic instrument comprising:

(a) a body, wherein the body defines a longitudinal axis, wherein the body is configured to receive an ultrasonic transducer;

(b) an actuation assembly, wherein the actuation assembly comprises:
  (i) at least one activation ring disposed coaxially with the longitudinal axis of the body, and
  (ii) at least one activation circuit, wherein the at least one activation circuit is associated with the at least one activation ring, wherein the at least one activation circuit is responsive to transverse movement of the at least one activation ring relative to the longitudinal axis of the body to transition between an open circuit condition and a closed circuit condition;

(c) a shaft assembly, wherein the shall assembly comprises an acoustic waveguide;

(d) an ultrasonic blade, wherein the ultrasonic blade is in acoustic communication with the acoustic waveguide, wherein the at least one activation circuit is operable to trigger activation of the acoustic waveguide; and (e) a biasing assembly configured to bias the at least one activation ring relative to the longitudinal axis toward the open circuit condition, wherein the biasing assembly comprises a spring encompassing a portion of the acoustic waveguide.

18. The ultrasonic instrument of claim 17, wherein the biasing assembly is configured to resiliently bias the at least one activation ring toward a position of coaxial alignment with the longitudinal axis of the body.

19. The ultrasonic instrument of claim 17, wherein the at least one activation ring includes a conductor, wherein the at least one circuit is in electrical communication with the conductor and at least a portion of the shaft assembly, wherein the at least one activation circuit is configured to transition to the closed circuit condition in response to movement of the at least one activation ring into contact with at least a portion of the shaft assembly.

20. An ultrasonic instrument comprising:

(a) a body, wherein the body defines a longitudinal axis, wherein the body is configured to receive an ultrasonic transduce;

(b) an actuation assembly, wherein the actuation assembly comprises;
  (i) an annular activation member assembly, wherein the annular activation member assembly comprises a first annular activation member and a second annular activation member, wherein the first and second annular activation members are disposed around the longitudinal axis of the body, wherein the second annular activation member is distal relative to the first activation member, and
  (ii) an activation circuit assembly, wherein the activation circuit assembly includes a first activation circuit and a second activation circuit, wherein the first activation circuit is associated with the first annular activation member, wherein the second activation circuit is associated with the second annular activation member, wherein the activation circuit assembly is configured to transition to an active state in response to lateral translation of the first annular activation member or the second annular activation member relative to the longitudinal axis of the body;

(c) a shaft assembly, wherein the shaft assembly comprises an acoustic waveguide;

(d) an ultrasonic blade, wherein the ultrasonic blade is in acoustic communication with the acoustic waveguide, wherein the activation circuit assembly is operable to trigger activation of the acoustic waveguide; and (e) a biasing assembly configured to bias the second activation member into a position that is coaxially aligned with the body, wherein the biasing assembly comprises an annular array of camming members extending through the first activation member.

\* \* \* \* \*